US012213995B2

(12) United States Patent
Pettine et al.

(10) Patent No.: US 12,213,995 B2
(45) Date of Patent: Feb. 4, 2025

(54) PREPARATIONS COMPRISING MESENCHYMAL STEM CELLS AND CANNABINOIDS AND METHODS OF THEIR USE

(71) Applicant: DIRECT BIOLOGICS, LLC, Austin, TX (US)

(72) Inventors: Kenneth Allen Pettine, Fort Collins, CO (US); Timothy Alexander Moseley, Fallbrook, CA (US)

(73) Assignee: DIRECT BIOLOGICS, LLC, Austin, TX (US)

( * ) Notice: Subject to any disclaimer, the term of this patent is extended or adjusted under 35 U.S.C. 154(b) by 409 days.

(21) Appl. No.: 17/628,011

(22) PCT Filed: Jul. 20, 2020

(86) PCT No.: PCT/US2020/042762
§ 371 (c)(1),
(2) Date: Jan. 18, 2022

(87) PCT Pub. No.: WO2021/011935
PCT Pub. Date: Jan. 21, 2021

(65) Prior Publication Data
US 2022/0257661 A1   Aug. 18, 2022

Related U.S. Application Data

(60) Provisional application No. 62/951,905, filed on Dec. 20, 2019, provisional application No. 62/875,889, filed on Jul. 18, 2019.

(51) Int. Cl.
*A61K 35/28* (2015.01)
*A61K 31/05* (2006.01)

(52) U.S. Cl.
CPC ............. *A61K 35/28* (2013.01); *A61K 31/05* (2013.01)

(58) Field of Classification Search
None
See application file for complete search history.

(56) References Cited

U.S. PATENT DOCUMENTS

| | | | |
|---|---|---|---|
| 3,610,795 A | 10/1971 | Antoine et al. | |
| 4,897,355 A | 1/1990 | Eppstein et al. | |
| 5,135,917 A | 8/1992 | Burch et al. | |
| 6,410,588 B1 | 6/2002 | Feldmann et al. | |
| 7,029,666 B2 | 4/2006 | Bruder et al. | |
| 8,021,882 B2 | 9/2011 | Johnstone et al. | |
| 8,057,789 B2 | 11/2011 | Hariri | |
| 8,372,797 B2 | 2/2013 | Ichim | |
| 8,703,710 B2 | 4/2014 | Dzau et al. | |
| 8,778,416 B2 | 7/2014 | Cohen | |
| 9,408,874 B2 | 8/2016 | Pettine | |
| 9,744,130 B2 | 8/2017 | Lipp et al. | |
| 9,856,455 B2 | 1/2018 | March et al. | |
| 9,980,984 B2 | 5/2018 | Pettine | |
| 10,456,425 B2 | 10/2019 | Herrera Sanchez et al. | |
| 10,744,160 B2 | 8/2020 | Sokolov et al. | |
| 10,881,693 B2 | 1/2021 | Alford | |
| 11,376,283 B2 | 7/2022 | Sokolov et al. | |
| 11,529,306 B2 | 12/2022 | Yi et al. | |
| 2004/0248970 A1* | 12/2004 | Webster | A61K 31/353 514/454 |
| 2007/0254827 A1* | 11/2007 | Sutton | A61K 31/137 514/1 |
| 2008/0241112 A1 | 10/2008 | Westenfelder | |
| 2009/0177487 A1 | 7/2009 | Eerkes | |
| 2010/0178274 A1 | 7/2010 | Sekiya et al. | |
| 2011/0003008 A1 | 1/2011 | Lim | |
| 2011/0014251 A1 | 1/2011 | Ray | |
| 2012/0064049 A1 | 3/2012 | Hunziker | |
| 2013/0115198 A1 | 5/2013 | Hoffmann et al. | |
| 2013/0195899 A1 | 8/2013 | Ichim et al. | |
| 2013/0210725 A1 | 8/2013 | Naughton et al. | |
| 2013/0236427 A1 | 9/2013 | Pernock | |
| 2014/0004601 A1 | 1/2014 | Lim | |
| 2014/0065240 A1 | 3/2014 | Mitsialis et al. | |
| 2014/0220053 A1 | 8/2014 | Muraca et al. | |
| 2015/0086513 A1 | 3/2015 | Savkovic et al. | |
| 2015/0125950 A1 | 5/2015 | Lim et al. | |
| 2016/0113967 A1 | 4/2016 | Hedrick et al. | |
| 2016/0263160 A1 | 9/2016 | Nolta et al. | |
| 2016/0281045 A1 | 9/2016 | McCall et al. | |
| 2017/0051359 A1 | 2/2017 | Pegtel et al. | |
| 2017/0055561 A1 | 3/2017 | Naughton et al. | |

(Continued)

FOREIGN PATENT DOCUMENTS

| | | | |
|---|---|---|---|
| AU | 2004203482 A1 | 8/2004 | |
| CA | 2880404 A1 | 2/2014 | |

(Continued)

OTHER PUBLICATIONS

PCT Form 326 Notification Concerning Transmittal of International Preliminary Report on Patentability issued in corresponding PCT Application No. PCT/US2020/042762, dated dated Jan. 27, 2022, 8 pages.
International Search Report and Written Opinion issued in corresponding PCT Application No. PCT/US2020/042762, dated Dec. 10, 2020, 11 pages.
Vuković, S., et al. "Cannabinoids and Pain: New Insights From Old Molecules," Frontiers in Pharmacology. vol. 9, 2018. https://www.frontiersin.org/article/10.3389/fphar.2018.01259.
Yang, X., et al. "Cannabidiol Regulates Gene Expression in Encephalitogenic T cells Using Histone Methylation and noncoding RNA during Experimental Autoimmune Encephalomyelitis," Sci Rep 9, 15780 (2019). https://doi.org/10.1038/s41598-019-52362-8.
Extended European Search Report received in corresponding European Application No. 20841625.5 mailed Jun. 28, 2023.

(Continued)

*Primary Examiner* — Blaine Lankford
(74) *Attorney, Agent, or Firm* — Wilson Sonsini Goodrich & Rosati

(57) ABSTRACT

Disclosed are compositions comprising a MSC secretome preparation and cannabinoids and methods of the use of said compositions for the treatment of inflammatory conditions.

8 Claims, 1 Drawing Sheet

(56) References Cited

U.S. PATENT DOCUMENTS

| | | |
|---|---|---|
| 2017/0107488 A1 | 4/2017 | Petcavich |
| 2017/0166864 A1 | 6/2017 | Kihm et al. |
| 2017/0189449 A1 | 7/2017 | Lim |
| 2017/0304368 A1 | 10/2017 | Marban et al. |
| 2018/0100149 A1 | 4/2018 | Marbán et al. |
| 2018/0214489 A1 | 8/2018 | Riordan |
| 2018/0264043 A1 | 9/2018 | Pettine et al. |
| 2018/0282762 A1 | 10/2018 | Gori |
| 2018/0318356 A1 | 11/2018 | Pettine et al. |
| 2018/0338866 A1 | 11/2018 | Kharazmi |
| 2019/0000886 A1 | 1/2019 | Ross |
| 2019/0015331 A1 | 1/2019 | Elliman et al. |
| 2019/0195863 A1 | 6/2019 | Brivanlou et al. |
| 2019/0209665 A1 | 7/2019 | Pluchino et al. |
| 2019/0269739 A1 | 9/2019 | Brodie et al. |
| 2019/0328792 A1 | 10/2019 | Traweger et al. |
| 2019/0330594 A1 | 10/2019 | You et al. |
| 2020/0030253 A1 | 1/2020 | Kharazmi |
| 2020/0316226 A1 | 10/2020 | Marban et al. |
| 2020/0325452 A1 | 10/2020 | Alford |
| 2021/0000882 A1 | 1/2021 | Coronado |
| 2021/0038652 A1 | 2/2021 | Naughton et al. |
| 2021/0169939 A1 | 6/2021 | Ilagan et al. |
| 2021/0196759 A1 | 7/2021 | Moseley et al. |
| 2021/0228643 A1 | 7/2021 | Bobis-Wozowicz et al. |
| 2021/0254056 A1 | 8/2021 | Liu et al. |
| 2021/0267892 A1 | 9/2021 | Machluf et al. |
| 2021/0299036 A1 | 9/2021 | Naughton |
| 2021/0348114 A1 | 11/2021 | Hudson et al. |
| 2021/0363525 A1 | 11/2021 | Saetrom et al. |
| 2021/0369617 A1 | 12/2021 | Alford |
| 2022/0000932 A1 | 1/2022 | Zhang et al. |
| 2022/0079987 A1 | 3/2022 | Pettine |
| 2022/0079990 A1 | 3/2022 | Moseley et al. |
| 2022/0096560 A1 | 3/2022 | Mitsialis et al. |
| 2022/0110970 A1 | 4/2022 | Jhan et al. |
| 2022/0125848 A1 | 4/2022 | Pettine et al. |
| 2022/0136011 A1 | 5/2022 | Kalluri |
| 2022/0136053 A1 | 5/2022 | Pettine et al. |
| 2022/0151934 A1 | 5/2022 | Ridall et al. |
| 2022/0152151 A1 | 5/2022 | Pettine |
| 2022/0175843 A1 | 6/2022 | Westenfelder et al. |
| 2022/0195384 A1 | 6/2022 | Kim et al. |
| 2022/0195390 A1 | 6/2022 | Uzan et al. |
| 2022/0202871 A1 | 6/2022 | Pettine |
| 2022/0218755 A1 | 7/2022 | Ilagan et al. |
| 2022/0249699 A1 | 8/2022 | Guild et al. |
| 2022/0264872 A1 | 8/2022 | March et al. |
| 2022/0273725 A1 | 9/2022 | Ochiya |
| 2022/0387518 A1 | 12/2022 | Mishra et al. |
| 2023/0000954 A1 | 1/2023 | Alford et al. |
| 2023/0002476 A1 | 1/2023 | Alford et al. |
| 2023/0013636 A1 | 1/2023 | Kalluri |
| 2023/0105667 A1 | 4/2023 | Brodie |
| 2023/0142496 A1 | 5/2023 | Cheng |
| 2023/0143893 A1 | 5/2023 | Bird et al. |
| 2023/0159932 A1 | 5/2023 | Pettine et al. |
| 2023/0172990 A1 | 6/2023 | Ohneda et al. |
| 2023/0181649 A1 | 6/2023 | Hariri et al. |
| 2023/0190818 A1 | 6/2023 | Jurga |
| 2023/0226267 A1 | 7/2023 | Madelska |
| 2023/0248773 A1 | 8/2023 | Jurga |
| 2023/0257712 A1 | 8/2023 | Jurga |
| 2023/0310507 A1 | 10/2023 | Lebovits et al. |
| 2023/0313191 A1 | 10/2023 | Hicok et al. |

FOREIGN PATENT DOCUMENTS

| | | |
|---|---|---|
| CN | 104622904 A | 5/2015 |
| CN | 108042572 A | 5/2018 |
| CN | 108498452 A | 9/2018 |
| CN | 111150743 A | 5/2020 |
| CN | 109718392 B | 11/2021 |
| EP | 2582791 A2 | 4/2013 |
| EP | 2687219 A1 | 1/2014 |
| EP | 2296672 B1 | 9/2015 |
| EP | 2683389 B1 | 5/2017 |
| EP | 2877187 B1 | 6/2019 |
| EP | 3492585 A1 | 6/2019 |
| EP | 3668319 A1 | 6/2020 |
| EP | 3672606 A1 | 7/2020 |
| EP | 3723773 A1 | 10/2020 |
| EP | 3402489 B1 | 6/2021 |
| EP | 3920889 A1 | 12/2021 |
| EP | 3952892 A1 | 2/2022 |
| EP | 4003305 A1 | 6/2022 |
| EP | 4069826 A1 | 10/2022 |
| EP | 4132546 A2 | 2/2023 |
| EP | 4181935 A1 | 5/2023 |
| JP | 2008544957 A | 12/2008 |
| JP | 2011513217 A | 4/2011 |
| JP | 2014500249 A | 1/2014 |
| JP | 2017180553 A | 10/2017 |
| JP | 2018538132 A | 12/2018 |
| JP | WO2019235362 A1 | 7/2021 |
| JP | 2022516607 A | 3/2022 |
| KR | 20180127280 A | 11/2018 |
| WO | WO-03051331 A1 | 6/2003 |
| WO | WO-2006036213 A2 | 4/2006 |
| WO | WO-2006071011 A1 | 7/2006 |
| WO | WO-2009105044 A1 | 8/2009 |
| WO | WO-2009150199 A1 | 12/2009 |
| WO | WO-2011160055 A2 | 12/2011 |
| WO | WO-2012061537 A2 | 5/2012 |
| WO | WO-2012125471 A1 | 9/2012 |
| WO | WO-2012142569 A2 | 10/2012 |
| WO | WO-2012174282 A2 | 12/2012 |
| WO | WO-2013006327 A1 | 1/2013 |
| WO | WO-2013090523 A2 | 6/2013 |
| WO | WO-2013159091 A2 | 10/2013 |
| WO | WO-2014005183 A1 | 1/2014 |
| WO | WO-2015031110 A2 | 3/2015 |
| WO | WO-2015048842 A1 | 4/2015 |
| WO | WO-2016082882 A1 | 6/2016 |
| WO | WO-2016149358 A1 | 9/2016 |
| WO | WO-2016156865 A1 | 10/2016 |
| WO | WO-2017001649 A1 | 1/2017 |
| WO | WO-2017023689 A1 | 2/2017 |
| WO | WO-2017076924 A1 | 5/2017 |
| WO | WO-2017117585 A1 | 7/2017 |
| WO | WO-2017122095 A1 | 7/2017 |
| WO | 2017139795 A1 | 8/2017 |
| WO | WO-2017196798 A1 | 11/2017 |
| WO | 2017218846 A1 | 12/2017 |
| WO | WO-2018038575 A1 | 3/2018 |
| WO | WO-2018078524 A1 | 5/2018 |
| WO | WO-2018083700 A1 | 5/2018 |
| WO | WO-2018102696 A1 | 6/2018 |
| WO | WO-2018130554 A1 | 7/2018 |
| WO | WO-2018131003 A1 | 7/2018 |
| WO | WO-2018131900 A2 | 7/2018 |
| WO | 2018144637 A1 | 8/2018 |
| WO | WO-2018150440 A1 | 8/2018 |
| WO | WO-2018162696 A1 | 9/2018 |
| WO | WO-2018208670 A1 | 11/2018 |
| WO | WO-2018226758 A2 | 12/2018 |
| WO | WO-2019035880 A1 | 2/2019 |
| WO | WO-2019040896 A1 | 2/2019 |
| WO | WO-2019099955 A1 | 5/2019 |
| WO | WO-2019118817 A1 | 6/2019 |
| WO | WO-2019143847 A1 | 7/2019 |
| WO | WO-2019152522 A1 | 8/2019 |
| WO | WO-2019161590 A1 | 8/2019 |
| WO | WO-2019217091 A1 | 11/2019 |
| WO | WO-2019222170 A1 | 11/2019 |
| WO | 2019231562 A1 | 12/2019 |
| WO | WO-2019235362 A1 | 12/2019 |
| WO | WO-2020021312 A1 | 1/2020 |
| WO | WO-2020061408 A1 | 3/2020 |
| WO | WO-2020081859 A1 | 4/2020 |
| WO | WO-2020139975 A1 | 7/2020 |
| WO | WO-2020142769 A1 | 7/2020 |
| WO | WO-2020160342 A1 | 8/2020 |
| WO | WO-2020163705 A1 | 8/2020 |

(56) References Cited

FOREIGN PATENT DOCUMENTS

| | | |
|---|---|---|
| WO | WO-2020163803 A1 | 8/2020 |
| WO | WO-2020172270 A1 | 8/2020 |
| WO | WO-2020182938 A1 | 9/2020 |
| WO | WO-2020210248 A1 | 10/2020 |
| WO | WO-2020223349 A1 | 11/2020 |
| WO | WO-2020230954 A1 | 11/2020 |
| WO | WO-2020251181 A1 | 12/2020 |
| WO | WO-2020257720 A1 | 12/2020 |
| WO | WO-2021009660 A1 | 1/2021 |
| WO | WO-2021011935 A1 | 1/2021 |
| WO | WO-2021016368 A1 | 1/2021 |
| WO | WO-2021016727 A1 | 2/2021 |
| WO | WO-2021113299 A1 | 6/2021 |
| WO | WO-2021113761 A1 | 6/2021 |
| WO | WO-2021147923 A1 | 7/2021 |
| WO | WO-2021177473 A1 | 9/2021 |
| WO | WO-2021181399 A1 | 9/2021 |
| WO | WO-2021195154 A1 | 9/2021 |
| WO | WO-2021207282 A2 | 10/2021 |
| WO | WO-2021216903 A1 | 10/2021 |
| WO | WO-2021221471 A1 | 11/2021 |
| WO | WO-2021226108 A1 | 11/2021 |
| WO | WO-2021262879 A1 | 12/2021 |
| WO | WO-2022008654 A1 | 1/2022 |
| WO | WO-2022008657 A1 | 1/2022 |
| WO | WO-2022018729 A1 | 1/2022 |
| WO | WO-2022050373 A1 | 3/2022 |
| WO | WO-2022076419 A1 | 4/2022 |
| WO | WO-2022096708 A1 | 5/2022 |
| WO | WO-2022150696 A1 | 7/2022 |
| WO | WO-2022174079 A1 | 8/2022 |
| WO | WO-2022190091 A1 | 9/2022 |
| WO | WO-2022251167 A2 | 12/2022 |
| WO | WO-2022261636 A1 | 12/2022 |
| WO | WO-2022265864 A2 | 12/2022 |
| WO | WO-2022266399 A1 | 12/2022 |
| WO | WO-2023004087 A2 | 1/2023 |
| WO | WO-2023275164 A1 | 1/2023 |
| WO | WO-2023278883 A1 | 1/2023 |
| WO | WO-2023281524 A1 | 1/2023 |
| WO | WO-2023282424 A1 | 1/2023 |
| WO | WO-2023021525 A1 | 2/2023 |
| WO | WO-2023024637 A1 | 3/2023 |
| WO | WO-2023033500 A1 | 3/2023 |
| WO | WO-2023064555 A1 | 4/2023 |
| WO | WO-2023075557 A1 | 5/2023 |
| WO | WO-2023082012 A1 | 5/2023 |
| WO | WO-2023091904 A1 | 5/2023 |
| WO | WO-2023123216 A1 | 7/2023 |
| WO | WO-2023127645 A1 | 7/2023 |
| WO | WO-2023192916 A2 | 10/2023 |
| WO | WO-2024192119 A1 | 9/2024 |

OTHER PUBLICATIONS

Libro et al. "Cannabidiol Modulates the Immunophenotype and Inhibits the Activation of the Inflammasome in Human Gingival Mesenchymal Stem Cells", Frontiers in Physiology, vol. 7, Nov. 24, 2016 (Nov. 24, 2016), XP093055410, CH ISSN: 1664-042X, DOI: 10.3389/fphys.2016.00559.
Rajan et al. "Cannabidiol Activates Neuronal Precursor Genes in Human Gingival Mesenchymal Stromal Cells", Journal of Cellular Biochemistry, vol. 118, No. 6, Dec. 29, 2016 (Dec. 29, 2016), pp. 1531-1546, XP093055405, Hoboken, USA ISSN: 0730-2312, DOI: 10.1002/jcb.25815 Retrieved from the Internet: URL:https://onlinelibrary.wiley.com/doi/full-XML/10.1002/jcb.25815.
Kim, "Mesenchymal Stem Cells vs. Mesenchymal Stem Cell Secretome for Rheumatoid Arthritis Treatment", JSM Arthritis, vol. 1, No. 1, Jan. 1, 2016 (Jan. 1, 2016), p. 1001, XP055578543.
Toh et al. "Advances in Mesenchymal Stem Cell-based Strategies for Cartilage Repair and Regeneration", Stem Cell Reviews and Reports, Humana Press Inc, US, vol. 10, No. 5, May 29, 2014 (May 29, 2014), pp. 686-696, XP035392625, ISSN: 1550-8943, DOI: 10.1007/S12015-014-9526-Z [retrieved on May 29, 2014].

Aatonen, Maria et al. Isolation and Characterization of Platelet-derived Extracellular Vesicles. Journal of Extracellular Vesicles 3:1-15 (2014).
Alam et al., An osteopontin-derived peptide inhibits human hair growth at least in part by decreasing fibroblast growth factor-7 production in outer root sheath keratinocytes. Br J Dermatol 182(6):1404-1414 (2020).
AU2019416339 Examination Report dated Sep. 16, 2024.
Aversa et al., Platelet-derived growth factor (PDGF) and PDGF receptors in rat corpus cavernosum: changes in expression after transient in vivo hypoxia. J Endocrinol. 170(2):395-402 (2001).
Backlund, Lena et al. Cognitive manic symptoms associated with the P2RX7 gene in bipolar disorder. Bipolar disorders 13(5-6):500-508 (2011).
Bagshawe, K. D., et al. A cytotoxic agent can be generated selectively at cancer sites. British Journal of Cancer 58(6):700-703 (1988).
Bagshawe, K. D. Towards generating cytotoxic agents at cancer sites. The First Bagshawe Lecture. Br. J. Cancer 60:275-281 (1989).
Ball et al., Arthroscopic treatment of post-traumatic elbow contracture. Journal of Shoulder and Elbow Surgery 11(6):624-629 (2002).
Barnett, J H, and J W Smoller. The genetics of bipolar disorder. Neuroscience 164(1):331-343 (2009).
Bassir, Seyed Hossein et al. Potential for Stem Cell-based Periodontal Therapy. Journal of Cellular Physiology 231(1):50-61 (2016).
Batch et al., Identification and localization of insulin-like growth factor-binding protein (IGFBP) messenger RNAs in human hair follicle dermal papilla. J Invest Dermatol. 106(3):471-475 (1996).
Battelli et al., T lymphocyte killing by a xanthine-oxidase-containing immunotoxin. Cancer Immunology, Immunotherapy 35(6):421-425 (1992).
Beitzel et al., The future role of mesenchymal stem cells in the management of shoulder disorders. Arthroscopy 29(10):1702-1711 (2013).
Bender et al.: Intra-Articular Injection of an Extracellular Vesicle Isolate to Treat Shoulder Osteoarthritis in an Athlete. J Regen Biol Med. 2(1):1-6 (2020).
Bender et al.: Treatment of Elbow Arthritis with a Bone Marrow derived Mesenchymal Stem Cell Extracellular Vesicle Isolate Product. J Orthop Study Sports Med. 1(1):1-6 (2021).
Bertolini et al., Abnormal interactions between perifollicular mast cells and CD8+ T-cells may contribute to the pathogenesis of alopecia areata. PLoS ONE. 9:e94260 (2014).
Biswas et al., Primary and secondary arthritis of the elbow. Arthritis. May 27, 2013 (2013).
Black et al., Effect of adipose-derived mesenchymal stem and regenerative cells on lameness in dogs with chronic osteoarthritis of the coxofemoral joints: a randomized, double-blinded, multicenter, controlled trial. Vet Ther 8:272-284 (2007).
Black et al., Effect of intraarticular injection of autologous adipose-derived mesenchymal stem and regenerative cells on clinical signs of chronic osteoarthritis of the elbow joint in dogs. Vet Ther. 9:192-200 (2008).
Bligh, Richard, and Robert Besancenez. Safety and Efficacy of Bone Marrow Mesenchymal Stem Cell Extracellular Vesicles in Long COVID Patients: A Case Series. Journal of Stem Cells Research Development & Therapy 10(1):1000112, 1-8 (2024).
Bligh: Treatment of Idiopathic Pulmonary Fibrosis With an Extracellular Vesicle Isolate Product. International Journal of Science and Research Archive. 02(02):231-236 (2021).
Blood And Marrow Stem Cell Transplantation. Leukemia & Lymphoma Society Retrieved from Internet URL: http://www.lls.org/resource-center/download-or-order-free-publications. Accessed on Jul. 8, 2016.
Boraschi CA, IL-18 in autoimmunity: review. Eur Cytokine Netw. 17:224-252 (2006).
Botchkarev et al., Edar signaling in the control of hair follicle development. J Investig Dermatol Symp Proc. 10(3):247-251 (2005).
BR2021012661 Office Action dated Sep. 3, 2024, and a partial English translation.
Brigham et al. Expression of a prokaryotic gene in cultured lung endothelial cells after lipofection with a plasmid vector. Am. J. Resp. Cell. Mol. Biol. 1:95-100 (1989).

(56) References Cited

OTHER PUBLICATIONS

Brown et al., Molecular and cellular mechanisms of receptor-mediated endocytosis. DNA and Cell Biology 10(6):399-409 (1991).
Burnett et al., GGF2 is neuroprotective in a rat model of cavernous nerve injury-induced erectile dysfunction. J Sex Med. 12(4):897-905 (2015).
Cabana: An Update on Exosomes. Aesthetic Authority. Technology Pipeline: Aestic Authority 2(1):22 (2020) https://www.dermatologytimes.com/view/an-update-on-exosomes.
Cai et al., Suppression of hepatocyte growth factor production impairs the ability of adipose-derived stem cells to promote ischemic tissue revascularization. Stem Cells 25(12):3234-3243 (2007).
Caplan et al., Mesenchymal stem cells as trophic mediators. J Cell Biochem 98:1076-1084 (2006).
Caplan et al., The MSC: an injury drugstore. Cell Stem Cell 9(1):11-5 (2011).
Carneiro et al., Emerging role for TNF-a in erectile dysfunction. J Sex Med. 7(12):3823-3834 (2010).
Celik et al., Genetic analysis of interleukin 18 gene polymorphisms in alopecia areata. J Clin Lab Anal. 32(5):e22386 (2018).
Centeno: Exosomes, Mary Kaye, and Pink Caddys (2019) https://regenexx.com/blog/direct-biologics-exosomes/.
Centers for Disease Control and Prevention (CDC) Prevalence and most common causes of disability among adults—United States, 2005. Morbidity and Mortality Weekly Report 58(16):421-426 (2009).
Chang et al., Exosomes and stem cells in degenerative disease diagnosis and therapy. Cell Transplantation 27(3):349-363 (2018).
Chang et al., Tissue engineering based cartilage repair with mesenchymal stem cells in a porcine model. J Orthop Res 29:1874-1880 (2011).
Chen et al., Regenerative hair waves in aging mice and extra-follicular modulators follistatin, dkk1, and sfrp4. J Invest Dermatol. 134(8):2086-2096 (2014).
Chen, Lei et al. Pre-vascularization Enhances Therapeutic Effects of Human Mesenchymal Stem Cell Sheets in Full Thickness Skin Wound Repair. Theranostics 7(1):117-131 (2017).
Cheng, Daye et al. The relationship between interleukin-18 polymorphisms and allergic disease: a meta-analysis. BioMed Research International 2014(1):290687, 1-11 (2014).
Cheng et al., Focus on mesenchymal stem cell-derived exosomes: opportunities and challenges in cell-free therapy. Stem Cells Int. 2017:6305295 (2017).
Chew et al., Mesenchymal stem cell exosomes enhance periodontal ligament cell functions and promote periodontal regeneration. Acta Biomater 15:89:252-264 (2019).
Chew et al., Mesenchymal stem cells in human meniscal regeneration: a systemic review. Ann Med Surg. 24:3-7 (2017).
Choi et al., Exosomes secreted by human adipose-derived stem cells regulate the expression of collagen synthesis-related genes in human dermal fibroblasts. Abstract Book: ISEV2017, Journal of Extracellular Vesicles 6:supl:1310414; PF11.07; 141-141 (2017).
Clinical Trial No. NCT04493242. Extracellular Vesicle Infusion Treatment for COVID-19 Associated ARDS. https://clinicaltrials.gov/study/NCT04493242 (Jul. 29, 2020).
Clinical Trial No. NCT04657458. Expanded Access for Use of bmMSC-Derived Extracellular Vesicles in Patients With COVID-19 Associated ARDS. https://clinicaltrials.gov/study/NCT04657458 (Dec. 7, 2020).
Clinical Trial No. NCT05116761. ExoFlo™ Infusion for Post-Acute COVID-19 and Chronic Post-COVID-19 Syndrome. https://clinicaltrials.gov/study/NCT05116761 (Nov. 9, 2021).
Clinical Trial No. NCT05125562. Extracellular Vesicles Infusion Treatment for Mild-to-Moderate COVID-19. https://clinicaltrials.gov/study/NCT05125562 (Nov. 16, 2021).
Clinical Trial No. NCT05127122. Bone Marrow Mesenchymal Stem Cell Derived Extracellular Vesicles Infusion Treatment for ARDS. https://clinicaltrials.gov/study/NCT05127122 (Nov. 9, 2021).
Clinical Trial No. NCT05130983. Study of ExoFlo for the Treatment of Medically Refractory Crohn's Disease. https://clinicaltrials.gov/study/NCT05130983 (Nov. 16, 2021).
Clinical Trial No. NCT05176366. Study of ExoFlo for the Treatment of Medically Refractory Ulcerative Colitis. https://clinicaltrials.gov/study/NCT05176366 (Dec. 14, 2021).
Clinical Trial No. NCT05215288. Expanded Access for Use of ExoFlo in Abdominal Solid Organ Transplant Patients https://clinicaltrials.gov/study/NCT05215288 (Jan. 18, 2022).
Clinical Trial No. NCT05354141. Extracellular Vesicle Treatment for Acute Respiratory Distress Syndrome (ARDS) (Extinguish ARDS). https://clinicaltrials.gov/study/NCT05354141 (Apr. 22, 2022).
Clinical Trial No. NCT05836883. Study of ExoFlo for the Treatment of Perianal Fistulas. https://clinicaltrials.gov/study/NCT05836883 (Apr. 19, 2023).
Conese et al.: Paracrine Effects and Heterogeneity of Marrow-Derived Stem/Progenitor Cells: Relevance for the Treatment of Respiratory Diseases. Cells Tissues Organs. 197:445-473 (2013).
Co-pending Appl. Serial No. PCT/US2019/026595 Application As Filed Apr. 9, 2019.
Co-pending Appl. Serial No. PCT/US2019/068615 Application As Filed Dec. 26, 2019.
Co-pending Appl. Serial No. PCT/US2020/012359 Application As Filed Jan. 6, 2020.
Co-pending Appl. Serial No. PCT/US2020/015982 Application As Filed Jan. 30, 2020.
Co-pending Appl. Serial No. PCT/US2020/017341 Application As Filed Feb. 7, 2020.
Co-pending Appl. Serial No. PCT/US2020/018821 Application As Filed Feb. 19, 2020.
Co-pending Appl. Serial No. PCT/US2020/030476 Application As Filed Apr. 29, 2020.
Co-pending Appl. Serial No. PCT/US2020/042762 Application As Filed Jul. 20, 2020.
Co-pending Appl. Serial No. PCT/US2021/028686 Application As Filed Apr. 22, 2021.
Co-pending Appl. Serial No. PCT/US2023/065115 Application As Filed Mar. 29, 2023.
Co-pending Appl. Serial No. PCT/US2024/019725 Application As Filed Mar. 13, 2024.
Co-pending Appl. Serial No. PCT/US2024/026444 Application As Filed Apr. 26, 2024.
Co-pending Appl. Serial No. PCT/US2024/033022 Application As Filed Jun. 7, 2024.
Co-pending Appl. Serial No. PCT/US2024/033123 Application As Filed Jun. 7, 2024.
Co-pending U.S. Appl. No. 17/059,874 Claims as of May 7, 2024.
Co-pending U.S. Appl. No. 17/418,342 Claims as of May 21, 2024.
Co-pending U.S. Appl. No. 17/420,500 Claims as of Jun. 13, 2024.
Co-pending U.S. Appl. No. 17/427,192 Claims as of Jun. 13, 2024.
Co-pending U.S. Appl. No. 17/429,553 Claims as of Aug. 9, 2021.
Co-pending U.S. Appl. No. 17/432,138 Claims as of Aug. 19, 2021.
Co-pending U.S. Appl. No. 17/606,514 Claims as of Oct. 26, 2021.
Co-pending U.S. Appl. No. 17/628,011 Claims as of Jan. 18, 2022.
Co-pending U.S. Appl. No. 17/920,997 Claims as of Oct. 24, 2022.
Co-pending U.S. Appl. No. 18/192,593 Claims as of Jun. 7, 2023.
Cosenza, et al. Mesenchymal stem cells derived exosomes and microparticles protect cartilage and bone from degradation in osteoarthritis. Sci Rep 7(1):16214, 1-12 (2017).
Crose et al.: Bone marrow mesenchymal stem cell-derived extracellular vesicle infusion for amyotrophic lateral sclerosis. Neurodegenerative Disease Management, 1-7 (2024).
Crose, Joshua J: Treating amyotrophic lateral sclerosis with a bone marrow derived mesenchymal stem cell extracellular vesicles. A case report. International Journal of Science and Research Archive. 02(02):167-171 (2021).
Cunningham et al., The therapeutic potential of the mesenchymal stem cell secretome in ischaemic stroke. J Cereb Blood Flow Metab. 38(8):1276-1292 (2018).
Database WPI Week 201851 Thomson Scientific, London, GB; AN 2018-41069T XP002807292, & CN 108 042 572 A (Beijing Doing Time Translational Medicin) May 18, 2018.
Database WPI Week 201877 Thomson Scientific, London, GB; AN 2018-724966 XP002807291, & CN 108 498 452 A (Univ Shanghai Second Med Renji Hospital) Sep. 7, 2018.

(56) References Cited

OTHER PUBLICATIONS

De Boeck, Astrid et al. Bone marrow-derived mesenchymal stem cells promote colorectal cancer progression through paracrine neuregulin 1/HER3 signalling. Gut 62(4):550-560 (2013). Online Published Apr. 25, 2012.
DeJong et al.: Extracellular vesicles: potential roles in regenerative medicine. Frontiers in Immunology. 5:608 (2014).
Direct Biologics, LLC Announces the Launch of ExoFlo Exosomes. Press Release (2019).
Direct Biologics Received FDA Approval to Initiate 'EXIT-COVID-19,' a Phase II Investigational New Drug Trial. (2020).
Dordevic et al., Intra-articular injection of an extracellular vesicle isolate product to treat hip labral tears. Journal of Regenerative Biology and Medicine 11:1-6 (2019).
Dreschnack, Paul A, and Ina Belshaku. Treatment of Idiopathic Facial Paralysis (Bell's Palsy) and Secondary Facial Paralysis With Extracellular Vesicles: a Pilot Safety Study. BMC Neurology 23(1):342, 1-9 (2023).
Dwyer et al., The acetabular labrum regulates fluid circulation of the hip joint during functional activities. Am J Sports Med. 42(4):812-819 (2014).
East et al.: Can IV Infusions Of Bone Marrow Derived Mesenchymal Stem Cell Extracellular Vesicles Be The Fountain Of Youth? Journal of Regenerative Biology and Medicine. 1(2):1-10 (2019).
East et al.: Intra-Articular Injection of an Extracellular Vesicle Isolate Product to Treat Hip Labral Tears. Journal of Regenerative Biology and Medicine. J Regen Biol Med. 2019;1(1):1-6 (2019).
East et al.: Intra-Articular Injection of an Extracellular Vesicle Isolate Product to Treat Knee Osteoarthritis in an Athlete. Journal of Biomedical Research and Clinical Investigation. 1(1):1005 (2020).
East et al.: IRB Approved Pilot Safety Study of an Extracellular Vesicle Isolate Product Evaluating the Treatment of Osteoarthritis in Combat-Related Injuries. Stem Cell Res. 1(2)-11 (2020).
East et al.: Pilot Safety Study of an Extracellular Vesicle Isolate Product for Treatment of Osteoarthritis in Combat-Related Injuries: One Year Follow Up. Genesis-JSCR-2(2)-21:1-10 (2021).
East et al.: The Safety Profile of a Bone Marrow-Derived Mesenchymal Stem Cell Extracellular Vesicle Isolate Product. J of Stem Cell Research. 6:026 (2020).
EP19906384.3 Extended European Search Report dated Aug. 29, 2022.
Epifanova et al., [Investigation of mechanisms of action of growth factors of autologous platelet-rich plasma used to treat erectile dysfunction]. Urologiia. Sep. 2017;(4):46-48 (2017) Russian. English Abstract Provided.
Erhardt et al., Association of polymorphisms in P2RX7 and CaMKKb with anxiety disorders. Journal of Affective Disorders 101(1-3):159-168 (2007).
Fan et al., Synovium-derived mesenchymal stem cells: a new source for musculoskeletal regeneration. Tissue Engineering Part B Review 15(1):75-86 (2009).
Felgner, Philip L, et al., Lipofection: A Highly Efficient, Lipid-Mediated DNA-Transfection Procedure. Proceedings of the National Academy of Sciences of the United States of America 84(21):7413-7417 (1987).
Feng et al. Transplantation of mesenchymal stem cells and nucleus pulposus cells in a degenerative disc model in rabbits: a comparison of 2 cell types as potential candidates for disc regeneration. J Neurosurgery Spine 14:322-329 (2011).
Ferrone et al.: Handbook of Monoclonal Antibodies. Noges Publications 22:303-357 (1985).
Fouad et al., Interleukin-18 gene polymorphisms in systemic lupus erythematosus: relation to disease status. Egypt J Immunol. 21:1-12 (2014).
Freitag et al., Mesenchymal stem cell therapy in the treatment of Osteoarthritis: reparative pathways,safety, and efficacy: a review. BMC Musculoskeletal Disorders 17:230 (2016).
Frisbie et al., Clinical update on the use of mesenchymal stem cells in equine orthopaedics. Equine Veterinary Journal, 42:86-89 (2010).

Fu, H et al., Identification of human fetal liver miRNAs by a novel method. FEBS letters 579(17):3849-3854 (2005).
Gao, Lei et al. Association of endothelial nitric oxide synthase polymorphisms with an increased risk of erectile dysfunction. Asian journal of andrology 19(3):330-337 (2017).
Gennaro, Alfonso R. Remington: The Science And Practice of Pharmacy, 19th Edition. Mack Publishing Company 1-6 (1995).
Gennaro, A.R., Remington: The science and practice of pharmacy. 19th edition. 1995. 12 Pages.
Gilhar A. Collapse of immune privilege in alopecia areata: coincidental or substantial? J Invest Dermatol. 130(11):2535-2537 (2010).
Giugliano et al., Erectile dysfunction associates with endothelial dysfunction and raised proinflammatory cytokine levels in obese men. J Endocrinol Invest. 27(7):665-669 (2004).
Guerico et al., Production of canine mesenchymal stem cells from adipose tissue and their application in dogs with chronic osteoarthritis of the humeroradial joints. Cell Biol Int 36:189-194 (2012).
Guo et al., Exosomes derived from platelet-rich plasma promote the re-epithelization of chronic cutaneous wounds via activation of YAP in a diabetic rat model. Theranostics 7(1):81-96 (2017).
Haber et al.: Biologic Effects of Specific Antibodies in Reversing the Pharmacologic and Toxic Effects of Digoxin. Raven Press 365-389(1977).
Hara, Tomonori et al. Genetics of bipolar disorder: insights into its complex architecture and biology from common and rare variants. Journal of human genetics 68(3):183-191 (2023). Published online May 26, 2022.
Harris JD. Hip labral repair: options and outcomes. Curr Rev Musculoskelet Med. 9(4):361-367 (2016).
Heijnen, Harry F. et al. Activated Platelets Release Two Types of Membrane Vesicles Microvesicles by Surface Shedding and Exosomes Derived From Exocytosis of Multivesicular Bodies and Alpha-granules. Blood 94(11)3791-3799 (1999).
Hessvik et al.: Current knowledge on exosome biogenesis and release description. Cell. Mol. Life Sci. 75:193-208 (2018).
Hicok et al.: Exosome Origins: Why the Cell Source Matters. Stem Cells Regen Med. 4(1):1-4 (2020).
Hiyama et al., Transplantation of mesenchymal stem cells in a canine disc degeneration model. J Orthop Res 26:589-600 (2008).
Ho, Chih-Yi. et al. Clinical and genetic aspects of alopecia areata: a cutting edge review. Genes 14(7):1362, 1-20 (2023).
Hotaling et al., DCCT/EDIC Research Group. Pilot genome-wide association search identifies potential loci for risk of erectile dysfunction in type 1 diabetes using the DCCT/EDIC study cohort. J Urol. 188(2):514-520 (2012).
Hou, Chun et al., Expression of matrix metalloproteinases and tissue inhibitor of matrix metalloproteinases in the hair cycle. Exp Ther Med. 12(1):231-237 (2016).
Howe et al.: The miracle of stem cells. Stemedica Cell Technologies, Inc. 202-210 (2011).
Hughes et al., Monoclonal antibody targeting of liposomes to mouse lung in vivo. Cancer Research 49(22):6214-6220 (1989).
Jacob et al., Association of the oxytocin receptor gene (OXTR) in caucasian children and adolescents with autism. Neuroscience Letters 417(1):6-9 (2007).
Jaeger et al., "Improved predictions of secondary structures for RNA", Proceedings of the National Academy of Sciences, vol. 86, No. 20, Oct. 1, 1989, pp. 7706-7710.
Jaeger, John A, et al., [17] Predicting optimal and suboptimal secondary structure for RNA. Methods in Enzymology 183:281-306 (1989).
Japanese Application No. 2021-537063 Office Action dated Dec. 15, 2023.
Japanese Application No. 2021-564403 Office Action dated May 30, 2024.
Johnston et al., A point mutation in PDGFRB causes autosomal-dominant Penttinen syndrome. Am J Hum Genet. 97(3):465-474 (2015).
Jorgenson, Eric et al. Genetic variation in the SIM1 locus is associated with erectile dysfunction. Proceedings of the National Academy of Sciences 115(43):11018-11023 (2018).
JP2021-517548 Office Action dated Apr. 4, 2023.

(56) References Cited

OTHER PUBLICATIONS

JP2021544344 Office Action dated Dec. 12, 2023, and an English translation.
JP2021546214 Office Action dated Dec. 19, 2023, and a partial English translation.
Julianto et al., Topical delivery of mesenchymal stem cells "secretomes" in wound repair. Acta Med Indones 48(3):217-220 (2016).
Kambur et al., Genetic variation in P2RX7 and pain tolerance. Pain 159(6):1064-1073 (2018).
Kandola et al., How does rheumatoid arthritis affect the wrists? Medical News Today https://www.medicalnewstoday.com/articles/323056 (2018).
Kavoussi et al., Recombinant PAI-1 therapy restores myoendothelial junctions and erectile function in PAI-1-deficient mice. Andrologia 47(10):1147-1152 (2015).
Kawabe et al., Localization of TIMP in cycling mouse hair. Development 111(4):877-879 (1991).
Kellgren et al., Radiological assessment of osteo-arthrosis. Ann Rheum Dis Dec. 16(4):494-502 (1957).
Kelly et al., Arthroscopic debridement without radial head excision of the osteoarthritic elbow. Arthroscopy 23(2):151-156 (2007).
Kim et al., Association between interleukin 18 polymorphisms and alopecia areata in Koreans. J Interferon Cytokine Res. 34:349-353 (2014).
Kim et al.: Wound healing effect of adipose-derived stem cells: A critical role of secretory factors on human dermal fibroblasts. Journal of Dermatological Science. 48:15-24 (2007).
Kinane, Denis F. et al. Periodontal diseases. Nature reviews Disease primers 3:17038, 1-14 (2017).
Koga et al., Synovial stem cells are regionally specified according to local microenvironments after implantation for cartilage regeneration. Stem Cells 25:689-696 (2007).
Koizumi et al., Distribution of IL-18 and IL-18 receptor in human skin: various forms of IL-18 are produced in keratinocytes. Arch Dermatol Res. 293(7):325-333 (2001).
Kondo, Ayano, and Tsuyoshi Osawa. Establishment of an Extracellular Acidic pH Culture System. Journal of Visualized Experiments 129:e56660, 1-7 (2017).
Krych et al., Modest mid-term outcomes after isolated arthroscopic debridement of acetabular tears. Knee Surg Sports Traumatol Arthrosc. 22(4):763-767 (2014).
Lai et al., Androgenic alopecia is associated with less dietary soy, higher blood vanadium and rs1160312 1 polymorphism in Taiwanese communities. PLos One 8(12):e79789, 1-11 (2013).
Lankford, Karen L, et al., Intravenously Delivered Mesenchymal Stem Cell-derived Exosomes Target M2-type Macrophages In The Injured Spinal Cord. PLoS One 13(1):e0190358, 20 Pages (2018).
Lecuyer et al., Dual role of ALCAM in neuroinflammation and blood-brain barrier homeostasis. Proc Natl Acad Sci U S A. 114(4):E524-E533 (2017).
Lee et al., Injectable mesenchymal stem cell therapy for large cartilage defects—a porcine model. Stem Cells 25:2964-2971 (2007).
Letsinger, Robert. L. et al. Cholesteryl-conjugated oligonucleotides: Synthesis, properties, and activity as inhibitors of replication of human immunodeficiency virus in cell culture. Proceedings of the National Academy of Sciences of the United States of America 86(17):6553-6556 (1989).
Levitte et al.: Mesenchymal stem cell-derived extracellular vesicles for the treatment of acute rejection in pediatric and adult bowl transplant. American Journal of Transplantation. 1-4 (2023).
Li, et al. Emerging Role of Exosomes in the Joint Diseases. Cell Physiol Biochem 47(5):2008-2017 (2018).
Li et al.: Mesenchymal stem cells and acellular products attenuate murine induced colitis. Stem Cell Research & Therapy. 11:515 (2020).
Li et al., Six novel susceptibility loci for early-onset androgenetic alopecia and their unexpected association with common diseases. PLoS Genetics 8(5):e1002746, 1-9 (2012).
Lichtenstein, A et al., Liposome-encapsulated silver sulfadiazine (SSD) for the topical treatment of infected burns: thermodynamics of drug encapsulation and kinetics of drug release. Journal of inorganic biochemistry 60(3):187-198 (1995).
Lightner, Amy L. et al. Bone Marrow Mesenchymal Stem Cell-Derived Extracellular Vesicle Infusion for the Treatment of Respiratory Failure From COVID-19: A Randomized, Placebo-Controlled Dosing Clinical Trial. Chest 164(6):1444-1453 (2023).
Lim et al.: Letter to the Editor re: "Exosomes Derived from Bone Marrow Mesenchymal Stem Cells as Treatment for Severe COVID-19" by Sengupta et al. Stem Cells and Development. 00(00) (2020).
Little et al., Total elbow arthroplasty: a systematic review of the literature in the English language until the end of 2003. Journal of Bone and Joint Surgery 87(4):437-444 (2005).
Litzinger et al., Biodistribution and immunotargetability of ganglioside-stabilized dioleoylphosphatidylethanolamine liposomes. Biochimica et Biophysica Acta (BBA)—Biomembranes 1104(1):179-187 (1992).
Liu et al., Prediction of male-pattern baldness from genotypes. European Journal of Human Genetics 24:895-902 (2015).
Lou, Danning et al. Single nucleotide polymorphisms in the non-coding region of STIM1 gene are associated with Parkinson disease risk in Chinese Han population. Medicine 99(9):e19234, 1-10 (2020).
Mancuso et al., Mesenchymal stem cell therapy for osteoarthritis: the critical role of the cell secretome. Front Bioeng Biotechnol 7:9 [1-9] (2019).
Marcinska et al., Evaluation of DNA variants associated with androgenetic alopecia and their potential to predict male pattern baldness. PLoS One 10(5):1-18, e0127852 (2015).
Massa et al.: Clinical Applications of Mesenchymal Stem/Stromal Cell Derived Extracellular Vesicles: Therapeutic Potential of an Accellular Product. Diagnostics. 10:999 (2020).
Mathieu et al.: Specificities of exosome versus small ectosome secretion revealed by live intracellular tracking of CD63 and CD9. Nat Commun. 12(4389):1-18 (2021).
Mazaheri et al., Ameliorating effect of osteopontin on H(2)O(2)-induced apoptosis of human oligodendrocyte progenitor cells. Cell Mol Neurobiol. 38(4):891-899 (2018).
Mcdowall et al., The role of activins and follistatins in skin and hair follicle development and function. Cytokine Growth Factor Rev. 19(5-6):415-426 (2008).
Mcquillin et al., Case-control studies show that a non-conservative amino-acid change from a glutamine to arginine in the P2RX7 purinergic receptor protein is associated with both bipolar- and unipolar-affective disorders. Molecular Psychiatry 14:614-620 (2008).
Messa, Genevieve E. et al. Treatment of a Recurrent Ischial Ulcer With Injected Exosomes. Journal of Surgical Case Reports 2022(6):rjac271, 1-3 (2022).
Mokbel et al., Homing and efficacy of intra-articular injection of autologous mesenchymal stem cells in experimental chondral defects in dogs. Clin Exp Rheumatol 29:275-284 (2011).
Monsel et al.: Mesenchymal Stem Cell Derived Secretome and Extracellular Vesicles for Acute Lung Injury and Other Inflammatory Lung Diseases. Expert Opin Biol Ther. 16(7):859-871 (2016).
Murphy et al., Stem cell therapy in a caprine model of osteoarthritis. Arthritis Rheum 48:3464-3474 (2003).
Needleman, Saul B, and Christian D Wunsch. A General Method Applicable to the Search for Similarities in the Amino Acid Sequence of Two Proteins. Journal of Molecular Biology 48(3):443-453 (1970).
Nguyen et al., Functional outcomes of arthroscopic capsular release of the elbow. Arthroscopy 22(8):842-849 (2006).
Ning et al., SNP@lincTFBS: an integrated database of polymorphisms in human LincRNA transcription factor binding sites. PLoS One 9(7):e103851, 1-8 (2014).
OHSU: Emergency Medicine Newsletter https://www.ohsu.edu/sites/default/files/2024-03/March%202024%20Newsletter%20%28Long%29.pdf (Mar. 2024).
Osborn et al.: A novel extracellular vesicle paradigm for the treatment of COVID-19 induced acute respiratory distress syndrome (ARDS). Respirator Medicine Case Reports. 51:102087 (2024).
Oyanguren-Desez et al., Gain-of-function of P2X7 receptor gene variants in multiple sclerosis. Cell Calcium 50(5):468-472 (2011).

(56) References Cited

OTHER PUBLICATIONS

Paicius, Rick et al. Safety and Efficacy of Intravenous ExoFlo in the Treatment of Complex Regional Pain Syndrome. Pain Physician 26(7):E851-E857 (2023).
Park et al., Hair growth stimulated by conditioned medium of adipose-derived stem cells is enhanced by hypoxia: evidence of increased growth factor secretion. Biomed Res. 31(1):27-34 (2010).
Patton, Mary C. et al. Hypoxia Alters the Release and Size Distribution of Extracellular Vesicles in Pancreatic Cancer Cells to Support Their Adaptive Survival. Journal of cellular biochemistry 121(1):828-839 (2021).
PCT/US2016/022629 International Preliminary Report on Patentability dated Sep. 28, 2017.
PCT/US2016/022629 International Search Report and Written Opinion dated Aug. 25, 2016.
PCT/US2019/026595 International Preliminary Report on Patentability dated Dec. 1, 2020.
PCT/US2019/026595 International Search Report and Written Opinion dated Jul. 2, 2019.
PCT/US2019/068615 International Search Report and Written Opinion dated Mar. 26, 2020.
PCT/US2020/012359 International Search Report and Written Opinion dated Mar. 24, 2020.
PCT/US2020/015982 International Preliminary Report on Patentability dated Aug. 12, 2021.
PCT/US2020/015982 International Search Report and Written Opinion dated Apr. 24, 2020.
PCT/US2020/017341 International Search Repot and Written Opinion dated Apr. 28, 2020.
PCT/US2020/018821 International Search Report and Written Opinion dated May 21, 2020.
PCT/US2020/030476 International Search Report and Written Opinion dated Aug. 12, 2020.
PCT/US2021/028686 International Search Report and Written Opinion dated Aug. 16, 2021.
PCT/US2023/065115 International Search Report and Written Opinion dated Sep. 27, 2023.
PCT/US2024/019725 International Search Report and Written Opinion dated Jun. 28, 2024.
PCT/US2024/019725 Invitation to Pay Additional Fees dated May 7, 2024.
PCT/US2024/026444 International Search Report and Written Opinion dated Jul. 15, 2024.
PCT/US2024/033022 International Search Report and Written Opinion dated Sep. 3, 2024.
Pearson, William R, and David J Lipman. Improved Tools For Biological Sequence Comparison. PNAS USA 85(8):2444-2448 (1988).
Pettine et al., Autogenous bone marrow concentrate for the treatment of osteoarthritis of the knee, hip and shoulder in former NFL players. J Stem Cell Res Ther. 4(1):9-13 (2018).
Pettine et al., Percutaneous injection of Autologous bone marrow concentrate significantly reduces lumbar discogenic pain through twelve months. Stem Cells 33:146-156 (2015).
Pettine et al., The biologic treatment of osteoarthritis with mesenchymal stem cell exosomes: the future is now. J Stem Cell Res Dev Ther. S1001:1-5 (2019).
Pettine et al., Tibial metaphyseal injection with bone marrow concentrate to treat knee arthritis. American J Stem Cell Res Ther. 2(1):5-10 (2018).
Pettine et al.: Treating Discogenic Pain with Mesenchymal Stem Cell Exosomes: What Is the Biologic Mechanism of Action. Jacobs Journal of Bone Marrow and Stem Cell Research. 5(1):017 (2019).
Philippon et al., The hip fluid seal—part I: the effect of an acetabularlabral tear, repair, resection, and reconstruction on hip fluid pressurization. Knee Surg Sports Traumatol Arthrosc. 22(4):722-729 (2014).
Phillips et aL: One month safety study of ExoFlo injection for the treatment of lumbar or cervical radiculopathy in the epidural space. International Journal of Science and Research Archive. 119-124 eISSN:2582-8185 (2021).
Phinney et al.: MSC-Derived Exosomes for Cell-Free Therapy. Stem Cells. 35:851-858 (2017).
Pietersz et al., Antibody conjugates for the treatment of cancer. Immunological Reviews 129(1):57-80 (1992).
Qi et al.: Exosomes Secreted by Human-Induced Pluripotent Stem Cell-Derived Mesenchymal Stem Cells Repair Critical-Sized Bone Defects through Enhanced Angiogenesis and Osteogenesis in Osteoporotic Rats. International Journal of Biological Sciences 12(7):836-849 (2016).
Qian et al., Vacuum therapy prevents corporeal veno-occlusive dysfunction and penile shrinkage in a cavernosal nerve injured rat model. Asian J Androl. 22(3):274-279 (2020).
Rhee, Sung-Mi et al. Injectable Tissue-engineered Soft Tissue for Tissue Augmentation. Journal of Korean Medical Science 29(Suppl3):S170-S175 (2014).
Roffler et al., Anti-neoplastic glucuronide prodrug treatment of human tumor cells targeted with a monoclonal antibody-enzyme conjugate. Biochemical Pharmacology 42(10):2062-2065 (1991).
RU2021122946 Examination Report dated Sep. 16, 2024.
Russian Patent Application No. 2021122956/10 Search Report issued on Jul. 6, 2023.
Saldanha-Araujo et al.: Mesenchymal Stem Cells: A New Piece in the Puzzle of COVID-19 Treatment. Frontiers in Immunology. 11:1563. (2020).
Salisbury et al.: SNP and haplotype variation in the human genome. Mutat Res 526(1-2):53-61 (2003).
Santos et al., Three-dimensional spheroid cell culture of umbilical cord tissue-derived mesenchymal stromal cells leads to enhanced paracrine induction of wound healing. Stem Cell Res Ther. 6(1):90 (2015).
Sasaki, Gordon H. Clinical Use of Extracellular Vesicles in the Management of Male and Female Pattern Hair Loss: A Preliminary Retrospective Institutional Review Board Safety and Efficacy Study. Aesthetic Surgery Journal. Open Forum 4:ojac045, 1-15 (2022).
Savoie et al., Arthroscopic management of the arthritic elbow: indications, technique, and results. Journal of Shoulder and Elbow Surgery 8(3):214-219 (1999).
Seldes et al., Anatomy, histologic features, and vascularity of the adult acetabular labrum. Clin Orthop Relat Res 2001(382):232-240 (2001).
Sengupta et al.: Exosomes Derived from Bone Marrow Mesenchymal Stem Cells as Treatment for Severe COVID-19. Stem Cells and Development. 29(12):747-754 (2020).
Sengupta et al.: Response to Lim et al. re "Exosomes Derived from Bone Marrow Mesenchymal Stem Cells as Treatment for Severe COVID-19". Stem Cells and Development. 29(14):879-881 (2020).
Senter et al., Generation of 5-fluorouracil from 5-fluorocytosine by monoclonal antibody-cytosine deaminase conjugates. Bioconjugate Chemistry 2(6):447-451 (1991).
Senter et al., Generation of cytotoxic agents by targeted enzymes. Bioconjugate Chemistry 4(1):3-9 (1993).
Sheinkop et al.: Intra-Articular Injection of an Extracellular Vesicle Isolate Product to Treat Hip Osteoarthritis. International Journal of Recent Scientific Research. 10(12A):36230-36232 (2019).
Shen et al., Four genetic variants interact to confer susceptibility to atopic dermatitis in Chinese Han population. Molecular Genetics and Genomics 290(4):1493-1498 (2015).
Singaporean Application No. 11202106836U Written Opinion dated Dec. 19, 2022.
Sivalingam et al., Single-nucleotide polymorphisms of the interleukin-18 gene promoter region in rheumatoid arthritis patients: protective effect of AA genotype. Tissue Antigens 62:498-504 (2003).
Skovronova, Renata. et al. Surface marker expresion in small and medium/large mesenchymal stromal cell-derived extracellular vesicles in naive or apoptotic condition using orthogonal techniques. bioRxiv. 1-32 (2021).

(56) References Cited

OTHER PUBLICATIONS

Smith et al., Isolation and implantation of autologous equine mesenchymal stem cells from bone marrow into the superficial digital flexor tendon as a potential novel treatment. Equine Vet J 35(1):99-102 (2003).
Smith et al., Mesenchymal stem cell therapy in equine tendinopathy. Disabil Rehabil 30:20-22, 1752-1758 (2008).
Smith, Temple F, and Waterman Michael S. Comparison of Biosequences. Advances in applied mathematics 2(4):482-489 (1981).
Spencer, Paige S, and Jose M Barral. Genetic Code Redundancy and Its Influence on the Encoded Polypeptides. Computational and Structural Biotechnology Journal 1:e201204006, 1-8 (2012).
Stevanato et al.: Investigation of Content, Stoichiometry and Transfer of miRNA from Human Neural Stem Cell Line Derived Exomes. PLoS ONE. 11(1):e0146353 (2016).
Suarez-Faritias et al., Alopecia areata profiling shows TH1, TH2, and IL-23 cytokine activation without parallel TH17/TH22 skewing. J Allergy Clin Immunol. 136(5):1277-1287 (2015).
Sun, JiaYang et al. The healing effects of conditioned medium derived from mesenchymal stem cells on radiation-induced skin wounds in rats. Cell transplantation 28(1):105-115 (2019).
Talegaonkar, The Role of Human MSC Derived Exosomes in the Treatment of Periodontal Diseases, Master's Thesis (2017).
Tamimi et al., Breast cancer susceptibility loci and mammographic density. Breast Cancer Research 10:R66 [1-9] (2008).
Thelen et al., Depending on its nano spacing, ALCAM promotes cell attachment and axon growth. PLoS One 7(12):e40493 (2012).
Toh, et al. MSC exosome as a cell-free MSC therapy for cartilage regeneration: Implications for osteoarthritis treatment. Seminars in Cell & Developmental Biology 67:56-64 (2017).
U.S. Appl. No. 17/059,874 Office Action dated Jul. 11, 2024.
U.S. Appl. No. 17/059,874 Restriction Requirement dated Nov. 8, 2023.
U.S. Appl. No. 17/418,342 Office Action dated Mar. 12, 2024.
U.S. Appl. No. 17/418,342 Office Action dated Sep. 5, 2024.
U.S. Appl. No. 17/420,500 Office Action dated Jul. 18, 2024.
U.S. Appl. No. 17/427,192 Office Action dated Apr. 17, 2024.
U.S. Appl. No. 17/432,138 Office Action dated Feb. 15, 2024.
U.S. Appl. No. 17/606,514 Office Action dated Sep. 16, 2024.
Vanamee et al., Structural principles of tumor necrosis factor superfamily signaling. Sci Signal. 11(511):eaao4910 (2018).
Vangsness et al., Adult human mesenchymal stem cells delivered via intra-articular injection to the knee following partial medial meniscectomy: a randomized, double-blind controlled study. J Bone Joint Surg Am. 96(2):90-98 (2014).
Vizoso et al.: Mesenchymal Stem CellSecretome: Toward Cell-Free Therapeutic Strategies in Regenerative Medicine.Int. J. Mol. Sci. 18:1852 (2017).
Vogel et al.: Clinical Practice Guideline for the Management of Anorectal Abscess, Fistula-in-Ano, and Rectovaginal Fistula. Dis Colon Recturm. 59(12):1117-1133 (2016).
Wang, et al. Exosomes from embryonic mesenchymal stem cells alleviate osteoarthritis through balancing synthesis and degradation of cartilage extracellular matrix. Stem Cell Res Ther 8(1):189, 1-13 (2017).
Wang et al., Macrophages induce AKT/beta-catenin-dependent Lgr5(+) stem cell activation and hair follicle regeneration through TNF. Nat Commun. 8:14091 (2017).
Wang et al., Upregulation of neuregulin-1 reverses signs of neuropathic pain in rats. Int J Clin Exp Pathol. 7(9):5916-5921 (2014).
Wang, Jiaqi et al. Exosomes: A Novel Strategy for Treatment and Prevention of Diseases. Frontiers in Pharmacology 8:300, 1-13 (2017).
Website: https://www.youtube.com/watch?v=0RtcsA5MQPs (2019).
Website: https://www.youtube.com/watch?v=8nvgzHzBRP0 (2021).
Website: https://www.youtube.com/watch?v=dNkcd3x1HBY (2020).
Website: https://www.youtube.com/watch?v=RaV2s6x-clg (2020).
Website: https://www.youtube.com/watch?v=V606jT6aHH0 (2021).
Weiss et al.: Letter to the Editor. Response to Sengupta et al. Stem Cells and Development. 29(24):1533-1534 (2020).
Wesselius et al., Association of P2X7 receptor polymorphisms with bone mineral density and osteoporosis risk in a cohort of Dutch fracture patients. Osteoporosis International 24(4):1235-1246 (2012).
Wilson, James E. et al. Safety of Bone Marrow Derived Mesenchymal Stem Cell Extracellular Vesicle Injection for Lumbar Facet Joint Pain. Regenerative Medicine 19(1):19-26 (2024).
Xia Xianfeng et al., Secretome from hypoxia-conditioned adipose-derived mesenchymal stem cells promotes the healing of gastric mucosal injury in a rodent model. Biochim Biophys Acta Mol Basis Dis 1864(1):178-188 (2018).
Yan et al., The platelet-derived growth factor receptor/STAT3 signaling pathway regulates the phenotypic transition of corpus cavernosum smooth muscle in rats. PLoS One 12(2):e0172191 (2017).
Yang et al., Effect of mesenchymal stem cells in autoimmune arthritis. Eur. J. Med. 34:130-137 (2018).
Yap, Chloe X. et al. Dissection of Genetic Variation and Evidence for Pleiotropy in Male Pattern Baldness. Nature communications 9(1):5407, 1-12 (2018).
Yepes, M. Urokinase-type plasminogen activator is a modulator of synaptic plasticity in the central nervous system: implications for neurorepair in the ischemic brain. Neural Regen Res. 15(4):620-624 (2020).
Yu et al.: Exosomes Derived from Bone Marrow Mesenchymal Stem Cells as Treatment for Severe COVID-19. Stem Cells & Dev. 29(12):747-754. doi:10.1089/scd.2020.0080 (2020).
Yu et al.: Exosomes Derived from Mesenchymal Stem Cells. Int. J. Mol. Sci. 15:4142-4157 (2014) doi:10.3390/ijms15034142.
Zhang, et al. Exosomes derived from human embryonic mesenchymal stem cells promote osteochondral regeneration. Osteoarthritis Cartilage 24(12):2135-2140 (2016).
Zhang et al., MSC exosomes mediate cartilage repair by enhancing proliferation, attenuating apoptosis and modulating immune reactivity. Biomaterials 156:16-27 (2018).
Zhao et al., NLRP3 inflammasome activation plays a carcinogenic role through effector cytokine IL-18 in lymphoma. Oncotarget 8(65):108571-108583 (2017).
Zhao et al., Stem cells for thetreatment of knee osteoarthritis: a comprehensive review. Pain Physician 21:229-241 (2018).
Zhou et al., Cross-talk between interferon-gamma and interleukin-18 in melanogenesis. J Photochem Photobiol B. 163:133-143 (2016).
Zhou et al., Effects of adipose-derived stem cells plus insulin on erectile function in streptozotocin-induced diabetic rats. Int Urol Nephrol. 48(5):657-669 (2016).
Zhou et al., Interleukin-18 augments growth ability of primary human melanocytes by PTEN inactivation through the AKT/NF-KB pathway. Int J Biochem Cell Biol. 45:308-331 (2013).
Zhu, et al. Comparison of exosomes secreted by induced pluripotent stem cell-derived mesenchymal stem cells and synovial membrane-derived mesenchymal stem cells for the treatment of osteoarthritis. Stem Cell Res Ther 8(1):64, 1-11 (2017).
Zinoviev et al.: Clinical evaluation of the effectiveness of mesenchymal stem cells in thermal burns. Bulletin of the National Medical and Surgical Center named after N.A. Pirogov. 13(4):Abstract (2018).
Zuker, M., On Finding All Suboptimal Foldings Of An RNA Molecule. Science 244(4900):48-52 (1989).

\* cited by examiner

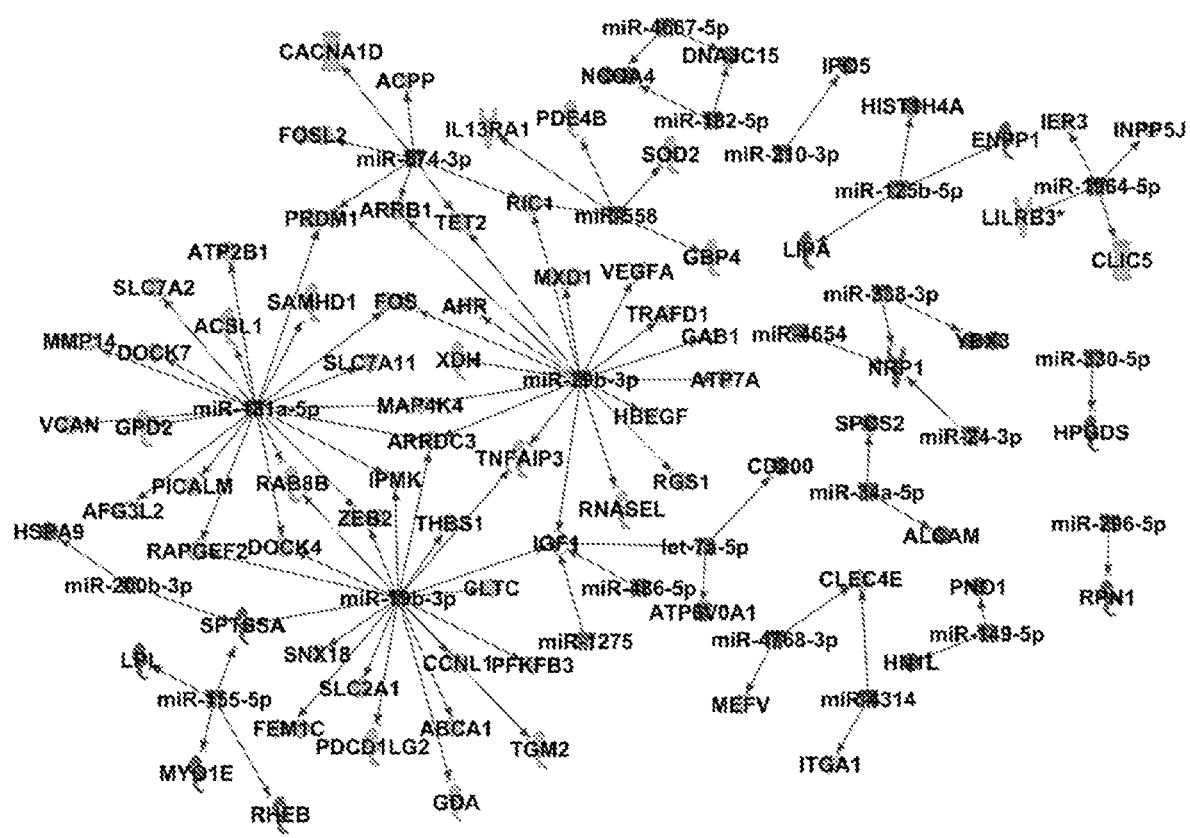

PREPARATIONS COMPRISING MESENCHYMAL STEM CELLS AND CANNABINOIDS AND METHODS OF THEIR USE

This is a national stage application filed under 35 U.S.C § 371 of PCT Application No. PCT/US2020/042762, entitled "PREPARATIONS COMPRISING MESENCHYMAL STEM CELLS AND CANNABINOIDS AND METHODS OF THEIR USE, and filed on Jul. 20, 2020 which claims the benefit of U.S. Provisional Application No. 62/951,905, filed on Dec. 20, 2019, and U.S. Provisional Application No. 62/875,889, filed on Jul. 18, 2019, applications which are incorporated herein by reference in their entireties.

I. BACKGROUND

Inflammation represents a fundamental mechanism of diseases caused by microbial, autoimmune, autoinflammatory, metabolic, and physical insults. Millions of people in the United States and globally suffer from inflammatory diseases. Inflammation is the body's response to harmful stimuli, and when limited, is beneficial and helps the body heal. However, when inflammation is unchecked it can lead to tissue destruction, necrosis, and fibrosis. For example, the action of microbial insults on microvascular endothelial cells in severe microbial infections evolving into their end stage, septic shock, leads to endothelial dysfunction that contributes to major organ failure, disseminated intravascular coagulation (DIC) involving liver microcirculation, acute respiratory distress syndrome (ARDS), acute kidney injury, and acute brain injury. Similarly, autoimmune factors targeting the body's own cells and organs develop into rampant inflammation, destroying skin and joints in psoriasis, lupus, and rheumatoid arthritis, and insulin-producing beta cells in Type 1 diabetes. Microbial and metabolic inflammation leads to insulin resistance, which underlies Type 2 diabetes. Chronic microbial inflammation caused by the oral microbiota of periodontitis, and bronchitis contribute to coronary heart disease while Hepatitis C virus infecting 200 million people worldwide contributes to fatty liver (steatosis), cirrhosis and, ultimately liver cancer.

Unfortunately, many inflammatory diseases are not adequately treated using conventional therapeutics. Steroidal anti-inflammatory drugs (e.g., hydrocortisone, prednisone, and methylprednisolone) have significant side effects increasing blood glucose, blood lipids and body fat distribution, skin thinning and delayed wound healing, muscle weakness, osteoporosis, increased susceptibility to infections, cataract, increased in eye pressure, stomach ulcers, and psychiatric disturbances. Methotrexate therapy is associated gastrointestinal and liver toxicity. Non-steroidal anti-inflammatory drugs (e.g., aspirin, ibuprofen, naproxen, celebrex) may cause fluid retention leading to edema, kidney failure (primarily with chronic use), liver failure, ulcers and prolonged bleeding after an injury or surgery. Inhibitors of kinases that target Bruton Tyrosine kinase (ibrutinib, acalabrutinib) and the JAK family of kinases may cause serious opportunistic infections with *Mycobacterium tuberculosis, Herpes zoster*, Cytomegalovirus, and *Pneumocystis jirovecii* pneumonia. Finally, monoclonal antibodies such as anti-TNFα monoclonal antibody carry the risk of the reactivation of latent infection with *Mycobacterium tuberculosis* and the monoclonal antibody natalizumab carries the risk of JC virus-caused progressive multifocal leukoencephalopathy in patients with multiple sclerosis. Thus, there is a need for more effective therapeutics for preventing and treating inflammation-mediated diseases.

II. SUMMARY

Disclosed are compositions comprising MSC secretome preparations and cannabinoids and methods of their use.

In one aspect disclosed herein are compositions comprising i) a mesenchymal stem cell (MSC) secretome preparation comprising MSC growth factors, MSC extracellular vesicles, MSC exosomes, and/or MSC extracts (including, but not limited to acellular MSC growth factors, MSC extracellular vesicles, MSC exosomes, and/or MSC extracts) and ii) a cannabinoid (such as, for example cannabidiol (CBD) and/or Cannabigerol (CBG)); wherein the growth factors, exosomes, extracts, and extracellular vesicles are obtained from cells selected from the group consisting of human MSCs, animal MSCs, multipotential stromal cells, fibroblasts, and fibroblast-like cells; and wherein the MSC preparation comprises at least one member selected from the group consisting of cells cultured under standard hyperoxyic culturing conditions and cells cultured under artificial wound healing conditions. For example, also disclosed herein are compositions of any preceding aspect, wherein the artificial wound healing conditions comprise about 0.1% to about 5% oxygen in the presence of inflammatory cytokines, angiogenic factors, and reduced glucose.

Also disclosed herein are methods of treating, inhibiting, reducing, ameliorating and/or preventing an inflammatory condition, an autoimmune disease, an autoinflammatory disease, metabolic disorder, or inflammation associated with any inflammatory condition, autoimmune disease, autoinflammatory disease, metabolic disorder, cancer, proliferative condition, injury, or microbial infection in a subject comprising administering to a subject a therapeutically effective amount of any of the compositions of any preceding aspect. For example, disclosed herein are methods of treating, inhibiting, reducing, ameliorating and/or preventing an inflammatory condition, an autoimmune disease, an autoinflammatory disease, metabolic disorder, or inflammation associated with any inflammatory condition, autoimmune disease, autoinflammatory disease, metabolic disorder, cancer, proliferative condition, injury, or microbial infection in a subject comprising administering to a subject a therapeutically effective amount of a mesenchymal stem cell (MSC) secretome preparation and a cannabinoid.

III. BRIEF DESCRIPTION OF THE DRAWINGS

The accompanying drawings, which are incorporated in and constitute a part of this specification, illustrate several embodiments and together with the description illustrate the disclosed compositions and methods.

FIG. 1 shows the expression pairing of differentially expressed genes and miRNAs in splenic CD4+ T cells in CBD treated EAE mice. Genes and miRNAs whose expression was significantly altered in MOG-induced EAE mice compared to nave mice were used for expression pairing by IPA analysis. Those induced by CBD treatment in EAE mice are shown red and those suppressed by CBD are shown green.

IV. DETAILED DESCRIPTION

Before the present compounds, compositions, articles, devices, and/or methods are disclosed and described, it is to be understood that they are not limited to specific synthetic methods or specific recombinant biotechnology methods unless otherwise specified, or to particular reagents unless otherwise specified, as such may, of course, vary. It is also to be understood that the terminology used herein is for the purpose of describing particular embodiments only and is not intended to be limiting.

A. DEFINITIONS

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

Ranges can be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data is provided in a number of different formats, and that this data, represents endpoints and starting points, and ranges for any combination of the data points. For example, if a particular data point "10" and a particular data point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

In this specification and in the claims which follow, reference will be made to a number of terms which shall be defined to have the following meanings:

"Optional" or "optionally" means that the subsequently described event or circumstance may or may not occur, and that the description includes instances where said event or circumstance occurs and instances where it does not.

An "increase" can refer to any change that results in a greater amount of a symptom, disease, composition, condition or activity. An increase can be any individual, median, or average increase in a condition, symptom, activity, composition in a statistically significant amount. Thus, the increase can be a 1, 2, 3, 4, 5, 6, 7, 8, 9, 10, 15, 20, 25, 30, 35, 40, 45, 50, 55, 60, 65, 70, 75, 80, 85, 90, 95, or 100% increase so long as the increase is statistically significant.

A "decrease" can refer to any change that results in a smaller amount of a symptom, disease, composition, condition, or activity. A substance is also understood to decrease the genetic output of a gene when the genetic output of the gene product with the substance is less relative to the output of the gene product without the substance. Also for example, a decrease can be a change in the symptoms of a disorder such that the symptoms are less than previously observed. A decrease can be any individual, median, or average decrease in a condition, symptom, activity, composition in a statistically significant amount. Thus, the decrease can be a 1, 2, 3, 4, 5, 6, 7, 8, 9, 10, 15, 20, 25, 30, 35, 40, 45, 50, 55, 60, 65, 70, 75, 80, 85, 90, 95, or 100% decrease so long as the decrease is statistically significant.

"Inhibit," "inhibiting," and "inhibition" mean to decrease an activity, response, condition, disease, or other biological parameter. This can include but is not limited to the complete ablation of the activity, response, condition, or disease. This may also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels.

By "reduce" or other forms of the word, such as "reducing" or "reduction," is meant lowering of an event or characteristic (e.g., tumor growth). It is understood that this is typically in relation to some standard or expected value, in other words it is relative, but that it is not always necessary for the standard or relative value to be referred to. For example, "reduces tumor growth" means reducing the rate of growth of a tumor relative to a standard or a control.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed.

The term "subject" refers to any individual who is the target of administration or treatment. The subject can be a vertebrate, for example, a mammal. In one aspect, the subject can be human, non-human primate, bovine, equine, porcine, canine, or feline. The subject can also be a guinea pig, rat, hamster, rabbit, mouse, or mole. Thus, the subject can be a human or veterinary patient.

The term "patient" refers to a subject under the treatment of a clinician, e.g., physician.

The term "therapeutically effective" refers to the amount of the composition used is of sufficient quantity to ameliorate one or more causes or symptoms of a disease or disorder. Such amelioration only requires a reduction or alteration, not necessarily elimination.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

"Biocompatible" generally refers to a material and any metabolites or degradation products thereof that are generally non-toxic to the recipient and do not cause significant adverse effects to the subject.

"Comprising" is intended to mean that the compositions, methods, etc. include the recited elements, but do not exclude others. "Consisting essentially of" when used to define compositions and methods, shall mean including the recited elements, but excluding other elements of any essential significance to the combination. Thus, a composition consisting essentially of the elements as defined herein would not exclude trace contaminants from the isolation and purification method and pharmaceutically acceptable carriers, such as phosphate buffered saline, preservatives, and the like. "Consisting of" shall mean excluding more than trace elements of other ingredients and substantial method steps for administering the compositions provided and/or claimed in this disclosure. Embodiments defined by each of these transition terms are within the scope of this disclosure.

A "control" is an alternative subject or sample used in an experiment for comparison purposes. A control can be "positive" or "negative."

"Effective amount" of an agent refers to a sufficient amount of an agent to provide a desired effect. The amount of agent that is "effective" will vary from subject to subject, depending on many factors such as the age and general condition of the subject, the particular agent or agents, and the like. Thus, it is not always possible to specify a quantified "effective amount." However, an appropriate "effective amount" in any subject case may be determined by one of ordinary skill in the art using routine experimentation. Also, as used herein, and unless specifically stated otherwise, an "effective amount" of an agent can also refer to an amount covering both therapeutically effective amounts and prophylactically effective amounts. An "effective amount" of an agent necessary to achieve a therapeutic effect may vary according to factors such as the age, sex, and weight of the subject. Dosage regimens can be adjusted to provide the optimum therapeutic response. For example, several divided doses may be administered daily or the dose may be proportionally reduced as indicated by the exigencies of the therapeutic situation.

A "pharmaceutically acceptable" component can refer to a component that is not biologically or otherwise undesirable, i.e., the component may be incorporated into a pharmaceutical formulation provided by the disclosure and administered to a subject as described herein without causing significant undesirable biological effects or interacting in a deleterious manner with any of the other components of the formulation in which it is contained. When used in reference to administration to a human, the term generally implies the component has met the required standards of toxicological and manufacturing testing or that it is included on the Inactive Ingredient Guide prepared by the U.S. Food and Drug Administration.

"Pharmaceutically acceptable carrier" (sometimes referred to as a "carrier") means a carrier or excipient that is useful in preparing a pharmaceutical or therapeutic composition that is generally safe and non-toxic and includes a carrier that is acceptable for veterinary and/or human pharmaceutical or therapeutic use. The terms "carrier" or "pharmaceutically acceptable carrier" can include, but are not limited to, phosphate buffered saline solution, water, emulsions (such as an oil/water or water/oil emulsion) and/or various types of wetting agents. As used herein, the term "carrier" encompasses, but is not limited to, any excipient, diluent, filler, salt, buffer, stabilizer, solubilizer, lipid, stabilizer, or other material well known in the art for use in pharmaceutical formulations and as described further herein.

"Pharmacologically active" (or simply "active"), as in a "pharmacologically active" derivative or analog, can refer to a derivative or analog (e.g., a salt, ester, amide, conjugate, metabolite, isomer, fragment, etc.) having the same type of pharmacological activity as the parent compound and approximately equivalent in degree.

"Therapeutic agent" refers to any composition that has a beneficial biological effect. Beneficial biological effects include both therapeutic effects, e.g., treatment of a disorder or other undesirable physiological condition, and prophylactic effects, e.g., prevention of a disorder or other undesirable physiological condition (e.g., a non-immunogenic cancer). The terms also encompass pharmaceutically acceptable, pharmacologically active derivatives of beneficial agents specifically mentioned herein, including, but not limited to, salts, esters, amides, proagents, active metabolites, isomers, fragments, analogs, and the like. When the terms "therapeutic agent" is used, then, or when a particular agent is specifically identified, it is to be understood that the term includes the agent per se as well as pharmaceutically acceptable, pharmacologically active salts, esters, amides, proagents, conjugates, active metabolites, isomers, fragments, analogs, etc.

"Therapeutically effective amount" or "therapeutically effective dose" of a composition (e.g. a composition comprising an agent) refers to an amount that is effective to achieve a desired therapeutic result. In some embodiments, a desired therapeutic result is the control of type I diabetes. In some embodiments, a desired therapeutic result is the control of obesity. Therapeutically effective amounts of a given therapeutic agent will typically vary with respect to factors such as the type and severity of the disorder or disease being treated and the age, gender, and weight of the subject. The term can also refer to an amount of a therapeutic agent, or a rate of delivery of a therapeutic agent (e.g., amount over time), effective to facilitate a desired therapeutic effect, such as pain relief. The precise desired therapeutic effect will vary according to the condition to be treated, the tolerance of the subject, the agent and/or agent formulation to be administered (e.g., the potency of the therapeutic agent, the concentration of agent in the formulation, and the like), and a variety of other factors that are appreciated by those of ordinary skill in the art. In some instances, a desired biological or medical response is achieved following administration of multiple dosages of the composition to the subject over a period of days, weeks, or years.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

B. COMPOSITIONS

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular MSC secretome preparation and cannabinoid composition is disclosed and discussed and a number of modifications that can be made to a number of molecules including the MSC secretome preparation and cannabinoid composition are discussed, specifically contemplated is each and every combination and permutation of MSC secretome preparation and cannabinoid composition and the modifications that are possible unless specifically indicated to the contrary. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

Mesenchymal stem cells (MSCs) have attracted much attention for their ability to regulate inflammatory processes. MSCs are important immunoregulatory cells in the body, because they respond to inflammation by homing to affected tissues and then controlling inflammation locally at that site. An essential characteristic of MSCs is their expression of a variety of chemokine and cytokine receptors that can home into the sites of inflammation by migrating towards inflammatory chemokines and cytokines. These MSCs carry out their immunomodulatory actions in several ways. MSCs regulate T-cell function, both in vitro and in vivo. MSCs can regulate an innate immune response by signaling dendritic cells to direct an anti-inflammatory T-cell response and by directly suppressing natural killer (NK) cell functions. Also, MSCs affect the adaptive immune response by the exertion of their immunoregulatory effects through direct interactions with T cells. These effects of MSCs occur in localized tissue environments, and therefore are not systemic. In addition, by recruiting endogenous stem cells to sites of injury as well as signal local stem cell differentiation, MSCs can promote tissue regeneration.

The primary trophic property of MSCs is the secretion of growth factors and exosomes to induce cell proliferation and angiogenesis. Exosomes express mitogenic proteins such as transforming growth factor-alpha (TGF-a), TGF-13, hepatocyte growth factor (HGF), epithelial growth factor (EGF), basic fibroblast growth factor (FGF-2) and insulin-like growth factor-I (IGF-I) to increase fibroblast, epithelial and endothelial cell division. Vascular endothelial growth factor (VEGF), IGF-I, EGF and angiopoietin-I are released to recruit endothelial lineage cells and initiate vascularization.

MSCs assist via paracrine mechanisms and modulate the regenerative environment via anti-inflammatory and immunomodulatory mechanisms. In response to inflammatory molecules such as interleukin-I (IL-I), IL-2, IL-12, tumor necrosis factor-a (TNF-a) and interferon-gamma (INF-γ), MSCs secrete an array of growth factors and anti-inflammatory proteins with complex feedback mechanisms among the many types of immune cells. The key immunomodulatory cytokines include prostaglandin 2, TGF-131, HGF, SDF-I, nitrous oxide, indoleamine 2, 3-dioxygenase, IL-4, IL-6, IL-I0, IL-I receptor antagonist and soluble tumor necrosis factor-a receptor. MSCs prevent proliferation and function of many inflammatory immune cells, including T-cells, natural killer cells, B-cells, monocytes, macrophages, and dendritic cells. Although MSCs across species are able to regulate T-cell activity, the mechanisms are not identical across mammalian species.

A characteristic of chronically inflamed environments is a persistent imbalance in the types of helper T-cells and macrophages. MSC exosomes indirectly promote the transition of TH1 to TH2 cells by reducing INF-γ and increasing IL-4 and IL-10. The restored TH1/TH2 balance has been shown to improve tissue regeneration in cartilage, muscle, and other soft tissue injuries, alleviate symptoms of autoimmune diseases, and have an anti-diabetic effect. Similarly, reduction in INF-γ and secretion of IL-4 promotes a shift in macrophages from M1 (proinflammatory, anti-angiogenic and tissue growth inhibition) to M2 (anti-inflammatory, proremodeling and tissue healing) type, an effect required for skeletal, muscular, and neural healing and regeneration.

Cannabinoid receptors and their endogenous ligands play a crucial role in the regulation of the immune system. There are two isotypes of cannabinoid (CB) receptors, CB I and CB2. These isoforms of cannabinoid receptors can be found throughout the human body in various organs and tissues. Cannabidiol has been shown to suppress T-cell-mediated immune responses by primarily inducing apoptosis and suppressing inflammatory cytokines and chemokines. Such observations indicate that targeting cannabinoid receptor-ligand interactions may constitute a novel window of opportunity to treat inflammatory and autoimmune disorders. As CB2 receptors are primarily expressed on immune cells, targeting CB2 may result in selective immunomodulation without overt toxicity. The future challenges for the use of cannabinoids as anti-inflammatory drugs include synthesis of cannabinoid receptor agonists that are non-psychoactive with anti-inflammatory activity and then identifying their mode of action. One such cannabinoid receptor agonist that is both nonpyschoactive and has anti-inflammatory activity is CBD as well as an affinity for both the CB1 and CB2 receptors.

Together, MSCs and CBD have a synergistic effect in regulating inflammation and the immune response as it is strongly suggested that CBD strongly regulates the proliferation, migration and neurogenesis of MSCs. Accordingly, disclosed herein are compositions acellular mesenchymal stem cell (MSC) derived growth factors, exosomes and cannabinoid (such as, for example CBD and/or CBG) for the treatment of various medical conditions.

C. MESENCHYMAL STEM CELLS

As noted throughout, the MSC and cannabinoid comprising compositions disclosed herein can utilize exosomes and/or growth factors derived from mesenchymal stem cells (MSCs). While existing autogenous and allogeneic MSCs contained within bone marrow, bone marrow concentrate, synovia-derived mesenchymal stem cells (MSCs), or adipose-derived stromal vascular fraction (SVF) or various post-natal products from umbilical cord, placenta or amnion, expanded MSC cultures are currently being used to treat wounds, orthopedic pathology, and spine pathology; the existing treatments do not contain large amounts of MSC secretomes (including, but not limited to growth factors, cytokines, chemokines, exosomes, extracellular vesicles, and/or extracts). Additionally, despite evidence in the art that treatments comprising stem cells (including injectable treatments) can help prevent aging and treat scarring, uneven pigmentation, existing skin products, such as creams, lotions, serums, make-up, and the like, while including ingredients that potentially help treat and strengthen the skin, other topical products do not penetrate the epidermis and more importantly do not include human MSCs, or MSC-derived growth factors and proteins. In fact, prior to the present disclosure an active MSC growth factor product that can be used for these applications has not been developed. Thus, in one aspect, disclosed herein are MSC secretome compositions (including, but not limited to MSC growth factor, MSC exosome, MSC extracts and/or extracellular vesicle comprising compositions (such as, for example, acellular MSC growth factors, MSC extracellular vesicles, MSC exosomes, and/or MSC extracts) for use in the treatment of wounds, orthopedic disorders, orthopedic injuries, ophthalmology, spinal injury, or spinal disorders, said treatment compositions comprising (i) a growth factor powdered additive comprising a mesenchymal stem cell (MSC)derived preparation and (ii) a pharmaceutically acceptable carrier.

As noted above, MSC are multipotent cells that have the ability to differentiate into a multitude of cell types including myocytes, chondrocytes, adipocytes, and osteoblasts. Typically, these cells can be found in the placenta, umbilical cord blood, adipose tissue, bone marrow, or amniotic fluid, including perivascular tissue. As used herein, "MSC" refers to non-terminally differentiated cells including but not limited to multipotential stem cell, multipotential stromal cell, stromal vascular cells, pericytes, perivascular cells, stromal cells, pluripotent cells, multipotent cells, adipose-derived fibroblast-like cells, adipose-derived stromal vascular fraction, adipose-derived MSC, bone marrow-derived fibroblast-like cells, bone marrow-derived stromal vascular fraction, bone marrow-derived MSC, tissue-derived fibroblast-like cells, adult stem cells, adult stromal cells, keratinocytes, and/or melanocytes.

It has been long recognized that MSC, in addition to their differentiation potential, have the immunomodulatory abilities resulting in the expression of many different cytokines and growth factors. As used herein, a "MSC preparation" or "MSC secretome composition" refers to a composition comprising MSC growth factors, MSC exosomes, extracellular vesicles, or acellular extracts of MSCs or MSC lysates obtained from human MSCs, fibroblast-like cells, and non-human animal MSCs including, but not limited to MSCs from horses, cows, pigs, sheep, non-human primates, dogs, cats, rabbits, rats, and mice. In embodiments, the MSCs may be derived from the patient to which the composition will be applied (autologous) or derived from another individual (allogeneic). The MSCs may be culture expanded to collect the conditioned media or to increase the quantity of cells for the lysate or used freshly prior to incorporation into the composition of the present disclosure.

The MSC secretome compositions (including, but not limited to MSC growth factor, MSC exosome, MSC extracts and/or extracellular vesicle comprising compositions (such as, for example, acellular MSC growth factors, MSC extracellular vesicles, MSC exosomes, and/or MSC extracts)) can comprise about 0.00001 to about 20 wt. %, such as from about 0.01 to about 10 wt. %, of a mesenchymal stem cell (MSC) extract, MSC exosome, or MSC growth factor preparation. The MSC preparation may comprise either MSC conditioned media or MSC lysate from cell culture expanded MSCs. In some embodiments, the composition may further comprise from about 0.01 to about 10 wt. % of a cell-free medium conditioned by growth of MSCs or MSC lineage cells, wherein the cells are cultured under normal hyperoxyic culturing conditions or under artificial wound healing conditions.

As disclosed herein the MSCs used to produce the disclosed MSC additives (including growth factor secretome composition either frozen or powdered additives) can be selectively stimulated to produce MSC growth factors, secretomes, cytokines, chemokines, mesenchymal stem cell proteins, peptides, glycosaminoglycans, extracellular matrix (ECM), proteoglycans, secretomes, and exosomes. As used herein, MSC growth factors include but are not limited to prostaglandin E2 (PGE2), transforming growth factor β1 (TGF-β1), hepatocyte growth factor (HGF), stromal cell derived factor-1 (SDF-1), nitric oxide, indoleamine 2,3-dioxygenase, interleukin-4 (IL-4), IL-6, interleukin-10 (IL-10), IL-1 receptor antagonist and soluble TNF-α receptor, insulin-like growth factors, fibroblast growth factors (FGF) 1-23 (especially, FGF1 and FGF2), bone morphogenetic proteins (BMPs) 1-15, epidermal growth factor (EGF), transforming growth factor-α (TGF-α) macrophage-stimulating protein (MSP), platelet derived growth factor (PLGF), vascular endothelial growth factor (VEGF), macrophage colony stimulating factor (M-CSF), insulin, granulocyte colony stimulating factor (G-CSF), granulocyte macrophage colony stimulating factor (GM-CSF), as well as hormones including estrogen, and thyroid hormones.

In one aspect, the MSC preparation (such as, for example, a MSC secretome composition) comprises MSC growth factors, MSC exosomes, and/or cellular extracts of MSCs or MSC lysates obtained from MSCs cultured under standard hyperoxyic culturing conditions (for example, 21% oxygen) or MSCs cultured under artificial wound healing conditions (such as, for example, 0.1% to about 5% oxygen in the presence of inflammatory cytokines, angiogenic factors, and reduced glucose).

As disclosed herein artificial wound healing conditions simulate growth conditions in real wounds where there is a reduction in nutrient supply and reduction of waste removal that is usually caused by a disruption in local blood circulation. This creates a harsh environment for cells until new blood vessels are created and blood circulation is restored. Accordingly, artificial wound healing conditions used to culture MSCs can include one or more of the following growth conditions reduction in glucose availability, reduction in oxygen tension, reduction in pH, and increased temperature.

In one aspect, the glucose availability can be reduced relative to normal control. Modified culture media to reduce glucose, but not damage the cells can be between 0 and 50% reduction in glucose, more preferably between about 5% and 40% reduction in glucose. For example, MSC artificial wound healing culture conditions can comprise glucose reduction of about 1, 2, 3, 4, 5, 6, 7, 8 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50% such as a glucose reduction from about 5% to about 15%, from about 10% to about 20%, from about 15% to about 25%, from about 20% to about 30%, or from about 25% to about 35%.

In one aspect, oxygen tension can be reduced to oxygen levels to hypoxic conditions. Normal atmospheric oxygen is approximately 21% and any reduction is considered hypoxic. Thus, in one aspect, MSCs can be cultured at between 0.0% and 20.9% oxygen, from about 0.1% to about 0.5% oxygen, from about 0.1% to about 2.0%, from about 0.1% to about 5.0% oxygen, from about 0.5% to 5.0%, from about 1.0% to about 10% oxygen, about 5.0% to about 10.0% oxygen; and from about 10.0% to about 15.0% under artificial wound healing conditions. Preferably during MSC would healing culture conditions oxygen tension is between about 0.5% and 20.5% oxygen, such as, for example, 0, 0.05, 0.1, 0.2, 0.3, 0.4, 0.5, 0.6, 0.7, 0.8, 0.9, 1.0, 1.1, 1.2, 1.3, 1.4, 1.5, 1.6, 1.7, 1.7, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10, 10.5, 11, 11.5, 12, 12.5, 13, 13.5, 14, 14.5, 15, 15.5, 16, 16.5, 17, 17.5, 18, 18.5, 19, 19.5, 20, or 20.5% oxygen.

The pH can also be reduced under artificial wound healing conditions. Physiologic pH is maintained very tightly and is usually very close to a neutral pH=7.2±0.2 (7.0-7.4). However, in a wound the acidic environment can have a pH=6.2±0.2 (i.e., a pH from 6.0 to about 6.4). Thus, under artificial wound healing culture conditions, pH can be from about 6.0 to about 7.4, for example, from 6.0 to about 6.4, from about 6.2 to about 6.4, from about 6.2 to about 6.6, from about 6.4 to about 6.6, from about 6.4 to about 6.8, or from about 6.6 to about 7.0, such as 6.0, 6.1, 6.2, 6.3, 6.4, 6.5, 6.6, 6.7, 6.8, 6.9, 7.0, 7.1, 7.2, 7.3 or 7.4.

Under artificial wound healing culture conditions, the temperature of the culture environment may be raised to simulate temperature increases at the site of a wound. Physiologic homeostasis temperature is maintained at 37° C. (98.6° F.). A slight increase or decrease can cause significant changes to cellular metabolism. By increasing the temperature above 37° C. to any temperature up to about 40° C. (104° F.) can create an "feverous" environment. Thus, in on aspect, the artificial wound healing culture conditions for the MSCs can comprise from about 35° C. to about 39° C., from about 35° C. to about 36° C., from about 36° C. to about 37° C., from about 37° C. to about 38° C., from about 38° C. to about 39° C., from about 39° C. to about 40° C. In one aspect, the temperature of the artificial wound healing culture can be 35.0, 35.1, 35.2, 35.3, 36.4, 35.5, 35.6, 35.7, 35.8, 35.9, 36.0, 36.1, 36.2, 36.3, 36.4, 36.5, 36.6, 36.7, 36.8, 36.9, 37.0, 37.1, 37.2, 37.3, 37.4, 37.5, 37.6, 37.7, 37.8, 37.9, 38.0, 38.1, 38.2, 38.3, 38.4, 38.5, 38.6, 38.7, 38.8, 38.9, 39.0, 39.1, 39.2, 39.3, 39.4, 39.5, 39.6, 39.7, 39.8, 39.9, or 40.0° C.

In one aspect, the MSC secretome compositions (including, but not limited to MSC growth factor, MSC exosome, MSC extracts and/or extracellular vesicle comprising compositions) can further comprise a protective coating (such as, for example, a cryoprotectant oligosaccharide and a protein solution) to reduce degradation of the growth factors. It is understood and herein contemplated that the protective coating can be engineered as a polymer. "Polymer" refers to a relatively high molecular weight organic compound, natural or synthetic, whose structure can be represented by a repeated small unit, the monomer. Non-limiting examples of polymers include polyethylene, rubber, cellulose. Synthetic polymers are typically formed by addition or condensation polymerization of monomers. The term "copolymer" refers to a polymer formed from two or more different repeating units (monomer residues). By way of example and without limitation, a copolymer can be an alternating copolymer, a random copolymer, a block copolymer, or a graft copolymer. It is also contemplated that, in certain aspects, various block segments of a block copolymer can themselves comprise copolymers. The term "polymer" encompasses all forms of polymers including, but not limited to, natural polymers, synthetic polymers, homopolymers, heteropolymers or copolymers, addition polymers, etc. In one aspect, the gel matrix can comprise copolymers, block copolymers, diblock copolymers, and/or triblock copolymers.

In one aspect, the protective coating can comprise a biocompatible polymer. In one aspect, biocompatible polymer can be crosslinked. Such polymers can also serve to slowly release the adipose browning agent and/or fat modulating agent into tissue. As used herein biocompatible polymers include, but are not limited to polysaccharides; hydrophilic polypeptides; poly(amino acids) such as poly-L-glutamic acid (PGS), gamma-polyglutamic acid, poly-L-aspartic acid, poly-L-serine, or poly-L-lysine; polyalkylene glycols and polyalkylene oxides such as polyethylene glycol (PEG), polypropylene glycol (PPG), and poly(ethylene oxide) (PEO); poly(oxyethylated polyol); poly(olefinic alcohol); polyvinylpyrrolidone); poly(hydroxyalkylmethacrylamide); poly(hydroxyalkylmethacrylate); poly(saccharides); poly(hydroxy acids); poly(vinyl alcohol), polyhydroxyacids such as poly(lactic acid), poly (gly colic acid), and poly (lactic acid-co-glycolic acids); polyhydroxyalkanoates such as poly3-hydroxybutyrate or poly4-hydroxybutyrate; polycaprolactones; poly(orthoesters); polyanhydrides; poly (phosphazenes); poly(lactide-co-caprolactones); polycarbonates such as tyrosine polycarbonates; polyamides (including synthetic and natural polyamides), polypeptides, and poly(amino acids); polyesteramides; polyesters; poly (dioxanones); poly(alkylene alkylates); hydrophobic polyethers; polyurethanes; polyetheresters; polyacetals; polycyanoacrylates; polyacrylates; polymethylmethacrylates; polysiloxanes; poly(oxyethylene)/poly(oxypropylene) copolymers; polyketals; polyphosphates; polyhydroxyvalerates; polyalkylene oxalates; polyalkylene succinates; poly (maleic acids), as well as copolymers thereof. Biocompatible polymers can also include polyamides, polycarbonates, polyalkylenes, polyalkylene glycols, polyalkylene oxides, polyalkylene terepthalates, polyvinyl alcohols (PVA), methacrylate PVA(m-PVA), polyvinyl ethers, polyvinyl esters, polyvinyl halides, polyvinylpyrrolidone, polyglycolides, polysiloxanes, polyurethanes and copolymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly (methyl methacrylate), poly(ethylmethacrylate), poly(butylmethacrylate), poly(isobutylmethacrylate), poly(hexlmethacrylate), poly(isodecylmethacrylate), poly(lauryl methacrylate), poly (phenyl methacrylate), poly (methyl acrylate), poly(isopropyl acrylate), poly(isobutyl acrylate), poly(octadecyl acrylate), polyethylene, polypropylene, poly(ethylene glycol), poly(ethylene oxide), poly (ethylene terephthalate), poly(vinyl alcohols), poly(vinyl acetate, poly vinyl chloride polystyrene and polyvinylpryrrolidone, derivatives thereof, linear and branched copolymers and block copolymers thereof, and blends thereof. Exemplary biodegradable polymers include polyesters, poly (ortho esters), poly(ethylene amines), poly(caprolactones), poly(hydroxybutyrates), poly(hydroxyvalerates), polyanhydrides, poly(acrylic acids), polyglycolides, poly(urethanes), polycarbonates, polyphosphate esters, polyphospliazenes, derivatives thereof, linear and branched copolymers and block copolymers thereof, and blends thereof.

In some embodiments the protective coating comprises carbohydrate construction of monosaccharides as well as carbohydrate polymers such as disaccharides or polysaccharides including but not limited to non-reducing poly or disaccharides as well as any combination thereof. Examples of carbohydrates that can be used in the protective coating comprise Glucose, Aldoses (D-Allose, D-Altrose, D-Mannose, etc.), Glucopyranose, Pentahydroxyhexanal, α-D-Glucopyranosyl-D-glucose, α-D-Glucopyranosyl-dihydrate, Polymer of β-D-Glycopyranosyl units, β-D-Fructofuranosyl α-D-glucopyranoside (anhydrous/dihydrate), β-D-Galactopyranosyl-D-glucose, α-D-Glucopyranosyl-α-D-glucopyranoside (anhydrous/dihydrate), Galactose, Pentoses (Ribose, xylose, lyxose), Dextrose, Dodecacarbon monodecahydrate, Fructose, Sucrose, Lactose, Maltose, Trehalose, Agarose, D-galactosyl-β-(1-4)-anhydro-L-galactosyl, Cellulose, Polymer of β-D-Glycopyranosyl units, and Starch, as well as, Polyhydric alcohols, Polyalcohols, Alditols, Erythritol, Glycitols, Glycerol, Xylitol, and Sorbitol.

In some embodiments the protective coating contains biocompatible and/or biodegradable polyesters or polyanhydrides such as poly(lactic acid), poly(glycolic acid), and poly(lactic-co-glycolic acid). The particles can contain one more of the following polyesters: homopolymers including glycolic acid units, referred to herein as "PGA", and lactic acid units, such as poly-L-lactic acid, poly-D-lactic acid, poly-D,L-lactic acid, poly-L-lactide, poly-D-lactide, and poly-D,L-lactide5 collectively referred to herein as "PLA", and caprolactone units, such as poly(e-caprolactone), collectively referred to herein as "PCL"; and copolymers including lactic acid and glycolic acid units, such as various forms of poly(lactic acid-co-glycolic acid) and poly(lactide-co-glycolide) characterized by the ratio of lactic acid:glycolic acid, collectively referred to herein as "PLGA"; and polyacrylates, and derivatives thereof. Exemplary polymers also include copolymers of polyethylene glycol (PEG) and the aforementioned polyesters, such as various forms of PLGA-PEG or PLA-PEG copolymers, collectively referred to herein as "PEGylated polymers". In certain embodiments, the PEG region can be covalently associated with polymer to yield "PEGylated polymers" by a cleavable linker. In one aspect, the polymer comprises at least 60, 65, 70, 75, 80, 85, 89, 90, 91, 92, 93, 94, 95, 96, 97, 98, or 99 percent acetal pendant groups.

The triblock copolymers disclosed herein comprise a core polymer such as, example, polyethylene glycol (PEG), polyvinyl acetate, polyvinyl alcohol, polyvinyl pyrrolidone (PVP), polyethyleneoxide (PEO), poly(vinyl pyrrolidone-co-vinyl acetate), polymethacrylates, polyoxyethylene alkyl ethers, polyoxyethylene castor oils, polycaprolactam, polylactic acid, polyglycolic acid, poly(lactic-glycolic) acid, poly(lactic co-glycolic) acid (PLGA), cellulose derivatives, such as hydroxymethylcellulose, hydroxypropylcellulose and the like.

Examples of diblock copolymers that can be used in the protective coatings disclosed herein comprise a polymer such as, example, polyethylene glycol (PEG), polyvinyl acetate, polyvinyl alcohol (PVA), polyvinyl pyrrolidone (PVP), polyethyleneoxide (PEO), poly(vinyl pyrrolidone-co-vinyl acetate), polymethacrylates, polyoxyethylene alkyl ethers, polyoxyethylene castor oils, polycaprolactam, polylactic acid, polyglycolic acid, poly(lactic-glycolic) acid, poly(lactic co-glycolic) acid (PLGA).

In one aspect, the protective coating contains (i.e., the encapsulated, the encapsulated compositions can further comprise lecithin or hydrolyzed lecithin as a carrier or as encapsulation material. As used herein, lecithin and/or hydrolyzed lecithin coatings include coatings comprising phosphatidyl choline, phosphatidyl inositol, phosphatidyl ethanolamine, phosphatidylserine, and phosphatidic acid. Sources of the lecithin can be pnat or animal sources.

In one aspect, any of the polymers, monosaccharides, disaccharides, or polysaccharides used to form the protective coating formed by placing the MSC additive in a encapsulating solution can be at an appropriate concentration for form the protective coating. For example, polymers, monosaccharides, disaccharides, or polysaccharides can be at any concentration between 0.01 mM and 10.0M concentration, for example, from about 0.01M to about 0.1M, from about 0.1 mM to about 1.0M, from about 1.0M to about 10.0M. Exemplary concentrations include 0.01, 0.02, 0.03, 0.04, 0.05, 0.06, 0.07, 0.08, 0.09, 0.1, 0.2, 0.3, 0.4, 0.4, 0.6, 0.7, 0.8, 0.9, 1, 2, 3, 4, 5, 6, 7, 8, 9, 10, 20, 30, 40, 50, 60, 70, 80, 90, 100, 110, 120, 130, 140, 150, 160, 170, 180, 190, 200, 225, 250, 275, 300, 325, 350, 375, 400, 450, 500, 600, 700, 800, 900 mM, 1, 1.1, 1.2, 1.3, 1.4, 1.5, 1.6, 1.7, 1.8, 1.9, 2, 3, 4, 5, 6, 7, 8, 9, 10M.

In one aspect, the treatment comprises MSC derived growth factors and exosomes comprise an MSC preparation (MSC/KIM/Prep) that includes at least one member selected from the group consisting of cells or cell conditioned media cultured under normal hyperoxic culturing conditions and cells cultured under harsh wound healing conditions. In some embodiments, Hyperoxic culturing conditions is defined as about 21%, wherein about 21% is 21%±5%, oxygen with serum supplements and oxygen, while wound healing conditions is defined as about 1 to about 5% oxygen in the presence of inflammatory cytokines, angiogenic factors, and/or reduced glucose.

In one aspect, acellular MSC growth factors and exosomes are derived from multiple sources such as bone marrow stroma, adipose, blood, dermis, periosteum, bone, and other tissues. In some embodiments, the acellular MSC growth factors and exosomes derived from the patient to which the composition will be applied (autologous) or derived from another individual (allogeneic). In alternative embodiments, the acellular MSC growth factors and exosomes are culture expanded to collect the conditioned media or to increase the quantity of cells for the lysate or used freshly prior to incorporation into the composition of the present disclosure.

As disclosed herein, in one aspect, the growth factors and exosomes can be derived from any cell in the human body including, but not limited to, ectodermal cells, endodermal cells, and/or mesodermal cells.

In alternative embodiments, the method further comprises including an at least one additive with the exosomes and growth factors.

D. CANNABINOIDS

As noted above, MSCs and CBD have a synergistic effect in regulating inflammation and the immune response as it is strongly suggested that CBD strongly regulates the proliferation, migration and neurogenesis of MSCs. Cannabinoid receptors and their endogenous ligands play a crucial role in the regulation of the immune system. There are two isotypes of cannabinoid (CB) receptors, CB I and CB2. These isoforms of cannabinoid receptors can be found throughout the human body in various organs and tissues. In some embodiment, the at least one cannabinoid is selected from the group consisting of Cannabichromene (CBC), Cannabichromenic acid (CBCA), Cannabichromevarin (CBCV), Cannabichromevarinic acid (CBCVA), Cannabicyclol (CBL), Cannabicyclolic acid (CBLA), Cannabicyclovarin (CBL V), Cannabidiol (CBD), Cannabidiol monomethylether (CBDM), Cannabidiolic acid (CBDA), Cannabidiorcol (CBD-Cl), Cannabidivarin (CBDV), Cannabidivarinic acid (CBDV A), Cannabielsoic acid B (CBEA-B), Cannabielsoin (CBE), Cannabielsoin acid A (CBEA-A), Cannabigerol (CBG), Cannabigerol monomethylether (CBGM), Cannabigerolic acid (CBGA), Cannabigerolic acid monomethylether (CB GAM), Cannabigerovarin (CB GV), Cannabigerovarinic acid (CBGV A), Cannabinodiol (CBND), Cannabinodivarin (CBVD), Cannabinol (CBN), Cannabinol methylether (CBNM), CannabinolC2 (CBN-C2), Cannabinol-C4 (CBN-C4), Cannabinolic acid (CBNA), Cannabiorcool (CBNC I), Cannabivarin (CBV), I 0-Ethoxy-9-hydroxy-delta-6a-tetrahydrocannabinol, 8,9-Dihydroxydelta-6a-tetrahydrocannabinol, Cannabitriol (CBT), Cannabitriolvarin (CBTV), Delta-8-tetrahydrocannabinol (118-THC), Delta-8-tetrahydrocannabinolic acid (118-THCA), Delta-9-tetrahydrocannabinol (THC), Delta-9-tetrahydrocannabinol-C4 (THC-C4), Delta-9-tetrahydrocannabinolic acid A (THCA-A), Delta-9-tetrahydrocannabinolic acid B (THCA-B), Delta-9-tetrahydrocannabinolic acid-C4 (THCA-C4), Delta-9-tetrahydrocannabiorcol (THC-CI), Del ta-9-tetrahydrocannabi or colic acid (THCA-C I), Delta-9-tetrahydrocannabi varin (THCV), Delta-9-tetrahydrocannabivarinic acid (THCV A), Delta-9-tetrahydrocannabinol (THC), Delta-9-tetrahydrocannabinol-C4 (THC-C4), Delta-9-tetrahydrocannabinolic acid A (THCA-A), Delta-9-tetrahydrocannabinolic acid B (THCA-B), Delta-9-tetrahydrocannabinolic acid-C4 (THCA-C4), Delta-9-tetrahydrocannabiorcol (THC-CI), Delta-9-tetrahydrocannabiorcolic acid (THCA-C I), Delta-9-tetrahydrocannabivarin (THCV), Delta-9-tetrahydrocannabivarinic acid (THCV A) and 3,4,5,6-Tetrahydro-7-hydroxy-alpha-alpha-2-trimethyl-9-n-propyl-2,6-methano-2H-1-benzoxocin-5-methanol. In alternative embodiments the cannabinoid is an isolate. In some embodiments the cannabinoid isolate is obtained by distillation process. In alternative embodiments, the cannabinoid isolate is dissolved in a solvent.

E. PHARMACEUTICAL CARRIERS/DELIVERY OF PHARMACEUTICAL PRODUCTS

As described above, the compositions can also be administered in vivo in a pharmaceutically acceptable carrier. By "pharmaceutically acceptable" is meant a material that is not biologically or otherwise undesirable, i.e., the material may be administered to a subject, along with the nucleic acid or vector, without causing any undesirable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The compositions may be administered orally, parenterally (e.g., intravenously (IV)), by intramuscular injection, by intraperitoneal injection, transdermally, extracorporeally, topically or the like, including topical intranasal administration or administration by inhalant. As used herein, "topical intranasal administration" means delivery of the compositions into the nose and nasal passages through one or both of the nares and can comprise delivery by a spraying mechanism or droplet mechanism, or through aerosolization of the nucleic acid or vector. Administration of the compositions by inhalant can be through the nose or mouth via delivery by a spraying or droplet mechanism. Delivery can also be directly to any area of the respiratory system (e.g., lungs) via intubation. The exact amount of the compositions required will vary from subject to subject, depending on the species, age, weight and general condition of the subject, the severity of the allergic disorder being treated, the particular nucleic acid or vector used, its mode of administration and the like. Thus, it is not possible to specify an exact amount for every composition. However, an appropriate amount can be determined by one of ordinary skill in the art using only routine experimentation given the teachings herein.

Parenteral administration of the composition, if used, is generally characterized by injection. Injectables can be prepared in conventional forms, either as liquid solutions or suspensions, solid forms suitable for solution of suspension in liquid prior to injection, or as emulsions. A more recently revised approach for parenteral administration involves use of a slow release or sustained release system such that a constant dosage is maintained. See, e.g., U.S. Pat. No. 3,610,795, which is incorporated by reference herein.

While allogenic cellular MSC IV infusion treatments have been widely pursued, there are numerous safety and regulatory concerns surrounding allogenic cellular preparations. The inherent problems with IV infusions of living MSCs include the trapping of the cells in the lungs, causing the cells to die within 24 hours. The cellular debris from this cell death ends up in the liver to be disposed. Current autogenous treatments from bone marrow concentrate only deliver a few thousand MSCs. While allogenic expanded MSC IV infusions can deliver hundreds of millions of living MSCs, they all get trapped in the lungs and die. The long-term effects of introducing the foreign DNA into the recipient is unclear and questions have arisen on whether introducing the large amount of foreign DNA could be carcinogenic. Accordingly, as noted above, administration of the compositions by inhalant can be through the nose or mouth via delivery by a spraying or droplet mechanism. Delivery can also be directly to any area of the respiratory system (e.g., lungs) via intubation.

By way of example, some embodiments of the present disclosure include a method for delivering mesenchymal stem cell (MSC) derived exosomes and growth factors by a pulmonary route of administration. In alternative embodiments, the method comprises inhaling a therapeutically effective dose of mesenchymal stem cell (MSCs) derived exosomes. In some embodiments, the method of inhaling is facilitated by pulmonary drug delivery devices. In alternative embodiments the pulmonary drug delivery device is a metered-dose inhaler. In some embodiments, the pulmonary drug delivery device is a pressurized metered-dose inhaler. In alternative embodiments, pulmonary drug delivery device is a dry powder inhaler. In some embodiments, the pulmonary drug delivery device is a nebulizer.

The materials may be in solution, suspension (for example, incorporated into microparticles, liposomes, or cells). These may be targeted to a particular cell type via antibodies, receptors, or receptor ligands. The following references are examples of the use of this technology to target specific proteins to tumor tissue (Senter, et al., *Bioconjugate Chem.*, 2:447-451, (1991); Bagshawe, K. D., *Br. J. Cancer*, 60:275-281, (1989); Bagshawe, et al., *Br. J. Cancer*, 58:700-703, (1988); Senter, et al., *Bioconjugate Chem.*, 4:3-9, (1993); Battelli, et al., *Cancer Immunol. Immunother.*, 35:421-425, (1992); Pietersz and McKenzie, *Immunolog. Reviews*, 129:57-80, (1992); and Roffler, et al., *Biochem. Pharmacol*, 42:2062-2065, (1991)). Vehicles such as "stealth" and other antibody conjugated liposomes (including lipid mediated drug targeting to colonic carcinoma), receptor mediated targeting of DNA through cell specific ligands, lymphocyte directed tumor targeting, and highly specific therapeutic retroviral targeting of murine glioma cells in vivo. The following references are examples of the use of this technology to target specific proteins to tumor tissue (Hughes et al., *Cancer Research*, 49:6214-6220, (1989); and Litzinger and Huang, *Biochimica et Biophysica Acta*, 1104:179-187, (1992)). In general, receptors are involved in pathways of endocytosis, either constitutive or ligand induced. These receptors cluster in clathrin-coated pits, enter the cell via clathrin-coated vesicles, pass through an acidified endosome in which the receptors are sorted, and then either recycle to the cell surface, become stored intracellularly, or are degraded in lysosomes. The internalization pathways serve a variety of functions, such as nutrient uptake, removal of activated proteins, clearance of macromolecules, opportunistic entry of viruses and toxins, dissociation and degradation of ligand, and receptor-level regulation. Many receptors follow more than one intracellular pathway, depending on the cell type, receptor concentration, type of ligand, ligand valency, and ligand concentration. Molecular and cellular mechanisms of receptor-mediated endocytosis has been reviewed (Brown and Greene, *DNA and Cell Biology* 10:6, 399-409 (1991)).

1. Pharmaceutically Acceptable Carriers

The compositions, including antibodies, can be used therapeutically in combination with a pharmaceutically acceptable carrier.

Suitable carriers and their formulations are described in Remington: *The Science and Practice of Pharmacy* (19th ed.) ed. A. R. Gennaro, Mack Publishing Company, Easton, PA 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8, and more preferably from about 7 to about 7.5. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. The compositions can be administered intramuscularly or subcutaneously. Other compounds will be administered according to standard procedures used by those skilled in the art.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, antiinflammatory agents, anesthetics, and the like.

The pharmaceutical composition may be administered in a number of ways depending on whether local or systemic treatment is desired, and on the area to be treated. Administration may be topically (including ophthalmically, vaginally, rectally, intranasally), orally, by inhalation, or parenterally, for example by intravenous drip, subcutaneous, intraperitoneal or intramuscular injection. The disclosed antibodies can be administered intravenously, intraperitoneally, intramuscularly, subcutaneously, intracavity, or transdermally.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable.

Compositions for oral administration include powders or granules, suspensions or solutions in water or non-aqueous media, capsules, sachets, or tablets. Thickeners, flavorings, diluents, emulsifiers, dispersing aids or binders may be desirable.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

In one aspect, the MSC secretome and cannabinoid compositions (including, but not limited to MSC growth factor, MSC exosome, MSC extracts and/or extracellular vesicle comprising compositions) disclosed herein may comprise any known ingredients typically found in the wound healing fields, such as oils, waxes or other standard fatty substances, or conventional gelling agents and/or thickeners; emulsifiers; moisturizing agents; emollients; sunscreens; hydrophilic or lipophilic active agents, such as ceramides; agents for combating free radicals; bactericides; sequestering agents; preservatives; basifying or acidifying agents; fragrances; surfactants; fillers; natural products or extracts of natural product, such as aloe or green tea extract; vitamins; or coloring materials. Other ingredients that may be combined with the powder may include an antioxidant, which can be selected from a variety of antioxidants. Suitable antioxidants include vitamins, such as Vitamin C (L-Ascorbate, Ascorbate-2 Phosphate magnesium salt, Ascorbyl Palmitate, Tetrahexyldecyl Ascorbate), Vitamin E (Tocotrienol), Vitamin A (retinol, retinal, retinoic acid, provitamin A carotenoids, such as beta-carotene), N-acetyl glucosamine, or other derivatives of glucosamine Other ingredients may include at least one essential fatty acid, such as Ω-3, Ω-6, and Ω-9 polyunsaturated fatty acids, such as linoleic acid (LA), gamma-linoleic acid (GLA), alpha-linoleic acid (ALA), dihomo-y-linolenic acid (DGLA), arachidonic acid (ARA), and others. The fatty acids may be derived from various sources including evening primrose oil, black currant oil, borage oil, or GLA modified safflower seeds. Other ingredients may include a platelet rich fibrin matrix, at least one ingredient to support ECM production and production of hyaluronic acid, such as N-acetyl glucosamine or other derivatives of glucosamine, ultra-low molecular weight (ULMW) hyaluronic acid, chondroitin sulfate, or keratin sulfate.

2. Therapeutic Uses

Effective dosages and schedules for administering the compositions may be determined empirically, and making such determinations is within the skill in the art. The dosage ranges for the administration of the compositions are those large enough to produce the desired effect in which the symptoms of the disorder are effected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counter indications. Dosage can vary, and can be administered in one or more dose administrations daily, for one or several days. Guidance can be found in the literature for appropriate dosages for given classes of pharmaceutical products. For example, guidance in selecting appropriate doses for antibodies can be found in the literature on therapeutic uses of antibodies, e.g., *Handbook of Monoclonal Antibodies*, Ferrone et al., eds., Noges Publications, Park Ridge, N.J., (1985) ch. 22 and pp. 303-357; Smith et al., *Antibodies in Human Diagnosis and Therapy*, Haber et al., eds., Raven Press, New York (1977) pp. 365-389. A typical daily dosage of the antibody used alone might range from about 1 µg/kg to up to 100 mg/kg of body weight or more per day, depending on the factors mentioned above.

F. METHOD OF TREATING INFLAMMATION, INFLAMMATORY DISEASES, AND AUTOIMMUNE DISEASE

The disclosed compositions can be used to treat any disease where inflammation is a cause or symptom that affects the health and well-being of the subject. As an example, inflammatory conditions may include metabolic syndrome (Syndrome X), diabetes, hyper fatty acidemia, inflammation, tissue injury, burns; inflammatory conditions where overactive cells, e.g., lymphocytes, macrophages, astrocytes, or microglia, strain the immune system, such as Parkinson's disease, Alzheimer's disease, Huntington's disease, multiple sclerosis (MS), Guillain-Barre syndrome (GBS), acute inflammatory demyelinating polyneuropathy, acute idiopathic polyradiculneuritis, acute idiopathic polyneuritis, or Landry's ascending paralysis), Lyme disease, Crohn's disease, ulcer, colitis, hemorrhoids, diarrhea, proctitis, arthritis osteoarthritis, rheumatoid arthritis, stroke, myocardial infarction, auricular or atrial fibrillation, preexcitation syndrome (Wolff-Parkinson-White syndrome), alcohol liver disease, arteriosclerosis, atherosclerosis, inflammation of blood vessels that characterize vascular disease in heart and brain, thromboangiitis obliterans (Winiwarter-Buerger disease). Thus, in one aspect, disclosed herein are methods of treating, inhibiting, reducing, ameliorating and/or preventing an inflammatory condition, an autoimmune disease, an autoinflammatory disease, metabolic disorder, or inflammation associated with any inflammatory condition, autoimmune disease, autoinflammatory disease, metabolic disorder, cancer, proliferative condition, injury, or microbial infection in a subject comprising administering to a subject a therapeutically effective amount of a mesenchymal stem cell (MSC) secretome preparation and a cannabinoid.

For example, in one aspect, disclosed herein are methods of treating, reducing, inhibiting, decreasing, ameliorating, and/or preventing an autoimmune disease in a subject or the symptoms associated with an autoimmune disease in a subject comprising administering to the subject a composition comprising an MSC secretome preparation and a cannabinoid (such as, for example CBD and/or CBG). As used herein, "autoimmune disease" refers to a set of diseases, disorders, or conditions resulting from an adaptive immune response (T cell and/or B cell response) against the host organism. In such conditions, either by way of mutation or other underlying cause, the host T cells and/or B cells and/or antibodies are no longer able to distinguish host cells from non-self-antigens and attack host cells bearing an antigen for which they are specific. Examples of autoimmune diseases include, but are not limited to graft versus host disease, transplant rejection, Achalasia, Acute disseminated encephalomyelitis, Acute motor axonal neuropathy, Addison's disease, Adiposis dolorosa, Adult Still's disease, Agammaglobulinemia, Alopecia areata, Alzheimer's disease, Amyloidosis, Ankylosing spondylitis, Anti-GBM/Anti-TBM nephritis, Antiphospholipid syndrome, Aplastic anemia, Autoimmune angioedema, Autoimmune dysautonomia, Autoimmune encephalomyelitis, Autoimmune enteropathy, Autoimmune hemolytic anemia, Autoimmune hepatitis, Autoimmune inner ear disease (AIED), Autoimmune myocarditis, Autoimmune oophoritis, Autoimmune orchitis, Autoimmune pancreatitis, Autoimmune polyendocrine syndrome, Autoimmune retinopathy, Autoimmune urticaria, Axonal & neuronal neuropathy (AMAN), Bal disease, Behcet's disease, Benign mucosal pemphigoid, Bickerstaff's encephalitis, Bullous pemphigoid, Castleman disease (CD), Celiac disease, Chagas disease, Chronic fatigue syndrome, Chronic inflammatory demyelinating polyneuropathy (CIDP), Chronic recurrent multifocal osteomyelitis (CRMO), Churg-Strauss Syndrome (CSS), Eosinophilic Granulomatosis (EGPA), Cicatricial pemphigoid, Cogan's syndrome, Cold agglutinin disease, Congenital heart block, Coxsackie myocarditis, CREST syndrome, Crohn's disease, Dermatitis herpetiformis, Dermatomyositis, Devic's disease (neuromyelitis optica), Diabetes mellitus type 1, Discoid lupus, Dressler's syndrome, Endometriosis, Enthesitis, Eosinophilic esophagitis (EoE), Eosinophilic fasciitis, Erythema nodosum, Essential mixed cryoglobulinemia, Evans syndrome, Felty syndrome, Fibromyalgia, Fibrosing alveolitis, Giant cell arteritis (temporal arteritis), Giant cell myocarditis, Glomerulonephritis, Goodpasture's syndrome, Granulomatosis with Polyangiitis, Graves' disease, Guillain-Barre syndrome, Hashimoto's encephalopathy, Hashimoto's thyroiditis, Hemolytic anemia, Henoch-Schonlein purpura (HSP), Herpes gestationis or pemphigoid gestationis (PG), Hidradenitis Suppurativa (HS) (Acne Inversa), Hypogammalglobulinemia, IgA Nephropathy, IgG4-related sclerosing disease, Immune thrombocytopenic purpura (ITP), Inclusion body myositis (IBM), Interstitial cystitis (IC), Inflamatory Bowel Disease (IBD), Juvenile arthritis, Juvenile diabetes (Type 1 diabetes), Juvenile myositis (JM), Kawasaki disease, Lambert-Eaton syndrome, Leukocytoclastic vasculitis, Lichen planus, Lichen sclerosus, Ligneous conjunctivitis, Linear IgA disease (LAD), Lupus nephritis, Lupus vasculitis, Lyme disease chronic, Meniere's disease, Microscopic polyangiitis (MPA), Mixed connective tissue disease (MCTD), Mooren's ulcer, Mucha-Habermann disease, Multifocal Motor Neuropathy (MMN) or MMNCB, Multiple sclerosis, Myasthenia gravis, Myositis, Narcolepsy, Neonatal Lupus, Neuromyelitis optica, Neutropenia, Ocular cicatricial pemphigoid, Optic neuritis, Ord's thyroiditis, Palindromic rheumatism (PR), PANDAS, Paraneoplastic cerebellar degeneration (PCD), Paroxysmal nocturnal hemoglobinuria (PNH), Parry Romberg syndrome, Pars planitis (peripheral uveitis), Parsonnage-Turner syndrome, Pemphigus, Peripheral neuropathy, Perivenous encephalomyelitis, Pernicious anemia (PA), POEMS syndrome, Polyarteritis nodosa, Polyglandular syndromes type I, II, III, Polymyalgia rheumatica, Polymyositis, Postmyocardial infarction syndrome, Postpericardiotomy syndrome, Primary biliary cirrhosis, Primary sclerosing cholangitis, Progesterone dermatitis, Psoriasis, Psoriatic arthritis, Pure red cell aplasia (PRCA), Pyoderma gangrenosum, Raynaud's phenomenon, Reactive Arthritis, Reflex sympathetic dystrophy, Relapsing polychondritis, Restless legs syndrome (RLS), Retroperitoneal fibrosis, Rheumatic fever, Rheumatoid arthritis, Rheumatoid vasculitis, Sarcoidosis, Schmidt syndrome, Schnitzler syndrome, Scleritis, Scleroderma, Sjögren's syndrome, Sperm & testicular autoimmunity, Stiff person syndrome (SPS), Susac's syndrome, Sydenham chorea, Sympathetic ophthalmia (SO), Systemic Lupus Erythematosus, Systemic scleroderma, Takayasu's arteritis, Temporal arteritis/Giant cell arteritis, Thrombocytopenic purpura (TTP), Tolosa-Hunt syndrome (THS), Transverse myelitis, Type 1 diabetes, Ulcerative colitis (UC), Undifferentiated connective tissue disease (UCTD), Urticaria, Urticarial vasculitis, Uveitis, Vasculitis, Vitiligo, Vogt-Koyanagi-Harada Disease, and Wegener's granulomatosis (or Granulomatosis with Polyangiitis (GPA)).

The MSC and cannabinoid compositions disclosed herein are not limited in their use for the treatment of inflammation resulting from adaptive immune responses, but are also effective in arresting inflammation-driven destruction associated with the inborn errors of innate immune responses (i.e. Constitutive inflammation that underlies autoinflammatory diseases). As used herein "autoinflammatory diseases refer to disorders where the innate immune response attacks host cells. Examples of autoinflammatory disorders include, Familial Cold Autoinflammatory Syndrome (FCAS), Muckle-Wells Syndrome (MWS), Neonatal-Onset Multisystem Inflammatory Disease (NOMID) (also known as Chronic Infantile Neurological Cutaneous Articular Syndrome (CINCA)), Familial Mediterranean Fever (FMF) and other cryopyrin-associated periodic syndromes (CAPS), Tumor Necrosis Factor (TNF)—Associated Periodic Syndrome (TRAPS), TNFRSF11A-associated hereditary fever disease (TRAPS11), Hyperimmunoglobulinemia D with Periodic Fever Syndrome (HIDS), Mevalonate Aciduria (MA), Mevalonate Kinase Deficiencies (MKD), Deficiency of Interleukin-1ß (IL-1ß) Receptor Antagonist (DIRA) (also known as Osteomyelitis, Sterile Multifocal with Periostitis Pustulosis), Majeed Syndrome, Chronic Nonbacterial Osteomyelitis (CNO), Early-Onset Inflammatory Bowel Disease, Diverticulitis, Deficiency of Interleukin-36-Receptor Antagonist (DITRA), Familial Psoriasis (PSORS2), Pustular Psoriasis (15), Pyogenic Sterile Arthritis, Pyoderma Gangrenosum, and Acne Syndrome (PAPA), Congenital sideroblastic anemia with immunodeficiency, fevers, and developmental delay (SIFD), Pediatric Granulomatous Arthritis (PGA), Familial Behçets-like Autoinflammatory Syndrome, NLRP12-Associated Periodic Fever Syndrome, Proteasome-associated Autoinflammatory Syndromes (PRAAS), Spondyloenchondrodysplasia with immune dysregulation (SPENCDI), STING-associated vasculopathy with onset in infancy (SAVI), Aicardi-Goutieres syndrome and other Type 1 Interferonopathies, Acute Febrile Neutrophilic Dermatosis, X-linked familial hemophagocytic lymphohistiocytosis, Lyn kinase-associated Autoinflammatory Disease (LAID), and intestinal and skin inflammatory disorders caused by deletion mutation of the carboxy-terminal segment of the NF-κB essential modulator (NEMO). In one aspect, disclosed herein are methods of treating an autoinflammatory disorder or inflammatory symptoms associated with an autoinflammatory disorder comprising administering to a subject with an autoinflammatory disease comprising administering to the subject a therapeutically effective amount of a composition a MSC secretome preparation and an cannabinoid (such as, for example CBD and/or CBG).

The novel MSc and cannabinoid immunotherapy described herein can arrest inflammation-driven organ injury, including damage resulting from metabolic disorders, such as, for example, metabolic syndrome that encompasses fatty liver, hypercholesterolemia, hypertriglyceridemia, diabetes mellitus, and obesity. Furthermore, Gaucher's disease, Phenylketonuria (PKU), Maple syrup urine disease (MSUD), hyperuricemia (gout), calcium pyrophosphate deposition disease (pseudo-gout), hyperthyroidism, hypothyroidism, dyslipidemia, hypolipidemia, and galactosemia). Thus, in one aspect, disclosed herein are methods of treating metabolic disease or metabolic disease mediated by inflammation comprising administering to a subject with a metabolic disease a therapeutically effective amount of a composition comprising a MSC secretome preparation and a cannabinoid (such as, for example CBD and/or CBG).

In one aspect, it is understood and herein contemplated that the immune response to any disease where uncontrolled cellular proliferation occurs such as metaplasia, dysplasia, cancers (i.e, malignant neoplasms) and benign neoplastic disorder can evolve from chronic inflammation and result in a significant organ injury mediated by inflammation. Thus, in one aspect disclosed herein are methods of treating an uncontrolled cellular proliferation including neoplastic conditions or cancers in a subject or symptoms associated with said conditions or cancers comprising administering to the subject a therapeutically effective amount of a composition comprising a MSC secretome preparation and a cannabinoid. As used herein more examples of neoplastic disorders and cancers that can be treated using the disclosed methods include but are not limited to lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, lung cancers such as small cell lung cancer and non-small cell lung cancer, neuroblastoma/glioblastoma, ovarian cancer, skin cancer, liver cancer, melanoma, squamous cell carcinomas of the mouth, throat, larynx, and lung, cervical cancer, breast cancer, and epithelial cancer, renal cancer, genitourinary cancer, lung cancer, esophageal carcinoma, head and neck carcinoma, large bowel cancer, hematopoietic cancers; testicular cancer; colon cancer, rectal cancer, prostatic cancer, and pancreatic cancer.

Many inflammatory conditions result from physical injuries mediated by inflammation (such as, for example abrasion, puncture, laceration, contusion, including brain trauma, blunt force trauma, ischemia, surgery, transplant, sunburn, chemical burn, high temperature burn, low temperature burn, radiation). Accordingly, in one aspect, disclosed herein are methods of treating inflammation caused by physical injury (such as, for example, abrasion, puncture, laceration, contusion, blunt force trauma, ischemia, surgery, transplant, sunburn, chemical burn, high temperature burn, low temperature burn) comprising administering to a subject with a physical injury a therapeutically effective amount of a composition comprising a MSC secretome preparation and a cannabinoid (such as, for example CBD and/or CBG).

In response to infection with a microbe such as, for example, a virus, bacterium, fungus, or parasite, the host immune system attempts to eliminate the infecting microbe by employing arms of the innate and adaptive immune systems including the production of cytokines, antibodies, and effector mechanisms of granulocyte, monocyte, macrophage, dendritic cell, innate lymphoid cells, NK cells, NK T cells, T cells, B cells, and plasma cells. Unchecked, this genomic reprogramming (genomic storm) leads to endothelial dysfunction, multi-organ failure and ultimately fatal shock, known as septic shock.

"Microbial inflammation" refers to a condition associated with its cardinal signs such as redness, swelling, increase in temperature, pain, and impairment of organ function such as disordered respiration as a result of the epithelial injury with adjacent microvascular endothelial injury in the lungs (and other organs) due to a microbial infection such as a virus, bacteria, fungi, or parasite. That is, "Microbial inflammation" is a mechanism of disease caused by infection ("microbial insult"). Microbial inflammation evolves from innate immune response to an infection due to a microbe such as, for example, a virus, bacterium, fungus, or parasite. Thus, the microbial injury caused by microbial virulence factors is aggravated by the host-produced inflammatory mediators that impede the clearance of invading microbes and add insult to organ's injury. It is understood and herein contemplated that the microbial inflammation and its end stage, sepsis can result from any microbial insult elicited by known (or unknown) virulence factors and microbial antigens.

The innate and adaptive immune response to infecting pathogen (disease-causing microorganism) can include the burst in production of cytokines, chemokines, and proteolytic enzymes by granulocytes, monocytes, macrophages, dendritic cells, mast cells, innate lymphoid cells, T cells, B cells, NK cells, and NK T cells. Microbial inflammation can be localized to a specific organ- or can be systemic. Microbial inflammation can proceed in stages from acute to subacute and chronic with attendant tissue destruction and subsequent fibrosis. Left unchecked, the acute microbial inflammation can lead to sepsis and septic shock, the end stage of microbial inflammation.

"Pathogen" is an agent that causes infection or disease, especially a virus, bacterium, fungus, protozoa, or parasite.

It is understood that the pathogen can be a virus. Thus in one embodiment the pathogen can be selected from the group consisting of Herpes Simplex virus-1, Herpes Simplex virus-2, Varicella-Zoster virus, Epstein-Barr virus, Cytomegalovirus, Human Herpes virus-6, Variola virus, Vesicular stomatitis virus, Hepatitis A virus, Hepatitis B virus, Hepatitis C virus, Hepatitis D virus, Hepatitis E virus, Rhinovirus, Coronavirus (including, but not limited to avian coronavirus (IBV), porcine coronavirus HKU15 (PorCoV HKU15), Porcine epidemic diarrhea virus (PEDV), HCoV-229E, HCoV-OC43, HCoV-HKU1, HCoV-NL63, SARS-CoV, SARS-CoV-2, or MERS-CoV), Influenza virus A, Influenza virus B, Measles virus, Polyomavirus, Human Papillomavirus, Respiratory syncytial virus, Adenovirus, Coxsackie virus, Chikungunya virus, Dengue virus, Mumps virus, Poliovirus, Rabies virus, Rous sarcoma virus, Reovirus, Yellow fever virus, Ebola virus, Marburg virus, Lassa fever virus, Eastern Equine Encephalitis virus, Japanese Encephalitis virus, St. Louis Encephalitis virus, Murray Valley fever virus, West Nile virus, Rift Valley fever virus, Rotavirus A, Rotavirus B, Rotavirus C, Sindbis virus, Simian Immunodeficiency virus, Human T-cell Leukemia virus type-1, Hantavirus, Rubella virus, Simian Immunodeficiency virus, Human Immunodeficiency virus type-1, and Human Immunodeficiency virus type-2.

Also disclosed are methods wherein the pathogen is a bacterium. The pathogen can be selected from the group of bacteria consisting of *Mycobacterium tuberculosis, Mycobacterium bovis, Mycobacterium bovis* strain BCG, BCG substrains, *Mycobacterium avium, Mycobacterium intracellular, Mycobacterium africanum, Mycobacterium kansasii, Mycobacterium marinum, Mycobacterium ulcerans, Mycobacterium avium* subspecies paratuberculosis, *Mycobacterium chimaera, Nocardia asteroides*, other *Nocardia* species, *Legionella pneumophila*, other *Legionella* species, Acetinobacter *baumanii, Salmonella typhi, Salmonella enterica*, other *Salmonella* species, *Shigella boydii, Shigella dysenteriae, Shigella sonnei, Shigella flexneri*, other *Shigella* species, *Yersinia pestis, Pasteurella haemolytica, Pasteurella multocida*, other *Pasteurella* species, *Actinobacillus pleuropneumoniae, Listeria monocytogenes, Listeria ivanovii, Brucella abortus*, other *Brucella* species, *Cowdria ruminantium, Borrelia burgdorferi, Bordetella avium, Bordetella pertussis, Bordetella bronchiseptica, Bordetella trematum, Bordetella hinzii, Bordetella pteri, Bordetella parapertussis, Bordetella ansorpii* other *Bordetella* species, *Burkholderia mallei, Burkholderia psuedomallei, Burkholderia cepacian, Chlamydia pneumoniae, Chlamydia trachomatis, Chlamydia psittaci, Coxiella burnetii*, Rickettsial species, *Ehrlichia* species, *Staphylococcus aureus, Staphylococcus epidermidis, Streptococcus pneumoniae, Streptococcus pyogenes, Streptococcus agalactiae, Escherichia coli, Vibrio cholerae, Campylobacter* species, *Neisseria meningitidis, Neiserria gonorrhea, Pseudomonas aeruginosa*, other *Pseudomonas* species, *Haemophilus influenzae, Haemophilus ducreyi*, other Hemophilus species, *Clostridium tetani*, other *Clostridium* species, *Yersinia* enterolitica, and other *Yersinia* species, and *Mycoplasma* species. In one aspect the bacteria is not *Bacillus anthracis*.

Also disclosed are methods wherein the pathogen is a fungus selected from the group of fungi consisting of *Candida albicans, Cryptococcus neoformans, Histoplasma* capsulatum, Aspergillus fumigatus, Coccidiodes immitis, Paracoccidioides brasiliensis, Blastomyces dermitidis, Pneumocystis carinii, Penicillium marneffi, and Alternaria alternata.

Also disclosed are methods wherein the pathogen is a parasite selected from the group of parasitic organisms consisting of Toxoplasma gondii, Plasmodium falciparum, Plasmodium vivax, Plasmodium malariae, other Plasmodium species, Entamoeba histolytica, Naegleria fowleri, Rhinosporidium seeberi, Giardia lamblia, Enterobius vermicularis, Enterobius gregorii, Ascaris lumbricoides, Ancylostoma duodenale, Necator americanus, Cryptosporidium spp., Trypanosoma brucei, Trypanosoma cruzi, Leishmania major, other Leishmania species, Diphyllobothrium latum, Hymenolepis nana, Hymenolepis diminuta, Echinococcus granulosus, Echinococcus multilocularis, Echinococcus vogeli, Echinococcus oligarthrus, Diphyllobothrium latum, Clonorchis sinensis; Clonorchis viverrini, Fasciola hepatica, Fasciola gigantica, Dicrocoelium dendriticum, Fasciolopsis bush, Metagonimus yokogawai, Opisthorchis viverrini, Opisthorchis felineus, Clonorchis sinensis, Trichomonas vaginalis, Acanthamoeba species, Schistosoma intercalatum, Schistosoma haematobium, Schistosoma japonicum, Schistosoma mansoni, other Schistosoma species, Trichobilharzia regenti, Trichinella spiralis, Trichinella britovi, Trichinella nelsoni, Trichinella nativa, and Entamoeba histolytica.

Accordingly, in one aspect, disclosed herein are methods of treating inflammation caused by microbial infection comprising administering to a subject with a microbial infection a therapeutically effective amount of a composition comprising a MSC secretome preparation and a cannabinoid (such as, for example CBD and/or CBG).

Thus, in one aspect, the methods disclosed herein include inhaling mesenchymal stem cells, MSC growth factors, and/or MSC exosomes by a patient. In some embodiments, the growth factors and exosomes are allogenic or autogenic.

In one aspect, it is understood and herein contemplated that the MSC secretome preparation and cannabinoid can be administered as separate administrations that occur sequentially, separate administrations that occur concurrently, separate administrations that occur simultaneously, or as single administrative dose composition. Thus, in one aspect, the MSC secretome composition can be administered 1, 2, 3, 4, 5, 6, 7, 8, 9, 10, 11, 12, 13, 14, 15, 20, 25, 30, 35, 40, 45, 50, 55, 60, 65, 70, 75, 80, 85, 90, 95, 100, 105, 110, 115, 120 min, 3, 4, 5, 6, 7, 8, 9, 10, 11, 12, 13, 14, 15, 16, 17, 18, 19, 20, 21, 22, 23, 24, 30, 36, 42, 48, 54, 60, 66, 72 hours, 4, 5, 6, 7, 8, 9, 10, 11, 12, 13, 14, 15, 16, 17, 18, 19, 20, 21, 22, 23, 24, 25, 26, 27, 28, 29, 30, 31, 32, 35, 42, 45, 49, 56, 58, 59, 60, 61, 62, 63, 90 days, 3, 4, 5, 6, 7, 8, 9, 10, 11, 12, 18, 24 months prior to administration of the cannabinoid or administered 1, 2, 3, 4, 5, 6, 7, 8, 9, 10, 11, 12, 13, 14, 15, 20, 25, 30, 35, 40, 45, 50, 55, 60, 65, 70, 75, 80, 85, 90, 95, 100, 105, 110, 115, 120 min, 3, 4, 5, 6, 7, 8, 9, 10, 11, 12, 13, 14, 15, 16, 17, 18, 19, 20, 21, 22, 23, 24, 30, 36, 42, 48, 54, 60, 66, 72 hours, 4, 5, 6, 7, 8, 9, 10, 11, 12, 13, 14, 15, 16, 17, 18, 19, 20, 21, 22, 23, 24, 25, 26, 27, 28, 29, 30, 31, 32, 35, 42, 45, 49, 56, 58, 59, 60, 61, 62, 63, 90 days, 3, 4, 5, 6, 7, 8, 9, 10, 11, 12, 18, 24 months following administration of the cannabinoid. As noted above, the cannabinoid and MSC secretome preparation can be administered concurrently, simultaneously, or as a combined single composition.

While it is appreciated that ideal effect will result in a single administration, many treatments are not so effective and can vary between individuals. Thus, in one aspect, disclosed herein are methods of treating, inhibiting, reducing, ameliorating and/or preventing an inflammatory condition, an autoimmune disease, an autoinflammatory disease, metabolic disorder, or inflammation associated with any inflammatory condition, autoimmune disease, autoinflammatory disease, metabolic disorder, cancer, proliferative condition, injury, or microbial infection in a subject comprising administering to the subject a therapeutically effective amount of a MSC preparation and a cannabinoid (including a composition comprising a MSC secretome preparation and a cannabinoid) 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more times, including regularly for the remaining lifetime of the subject or until the underlying inflammatory condition, an autoimmune disease, an autoinflammatory disease, metabolic disorder, or inflammation associated with any inflammatory condition, autoimmune disease, autoinflammatory disease, metabolic disorder, cancer, proliferative condition, injury, or microbial infection is cured. The frequency of administration can occur once every 4, 6, 12, 18, 24, 48, 72 hours, 4, 5, 6, 7 days, 2, 3, 4, 5, 6, 7, 8, 9 weeks, 3, 4, 5, 6, 7, 8, 9, 10, 11, 12, 18, 24, 36, 48 months

G. EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Hypoxic/nutrient deficient stress induced extracelluar vesicles (EVs) from bone-marrow mesenchymal stem/stromal cells contains both proteins and micro-ribonucleic acid regulatory sequences (miRNAs) that work synergistically with CBD or other cannabinoid agonists (CAs) to effect positive reduction or reversal of symptoms in autoimmune and chronic pain diseases. Two mechanisms of interactivity of the combined therapeutic invention can cause this effect.

BM-MSC secreted EVs and proteins (collectively "the secretome") can work synergistically with cannabinoid agonists contributing additional protein content to target cells with which CAs interact. For example, in a murine model of experimental autoimmune encephalitogenic (EAE), the cannabinoid agonist CBD interacts with T cells that are believed to be responsible for generating the disease (Yang et al Nature 2019). Proteins and micro RNAs that were altered by CBD were identified and the interactional relationships of these molecules were mapped. FIG. 1.

Proteomic analysis of the BM-MSC secretome protein content of the MSC secretome preparation was performed. Proteins identified as present within the MSC secretome preparation were compared to the proteins in FIG. 1 that were shown to be upregulated by CBD. Two proteins were identified to be present in both lists (Table 1).

TABLE 1

Proteins expressed that synergistically improve CAs effects in autoimmunity.

| Protein ID | Relevant Function and MoA that support CBD |
|---|---|
| ALCAM | Relevant to relief of EAE symptoms: Is a membrane protein required for stem cell engraftment and appropriate development of white blood cells in the bone marrow. Promotes regulatory T cell activation and proliferation (PubMed: 24740813) Relevant to relief of chronic Pain from inflammation destruction of nerves: AlCAM promotes neurite extension, axon growth and axon guidance; axons grow preferentially on surfaces that contain ALCAM. Mediates outgrowth and pathfinding for retinal ganglion cell axons (By similarity) |
| CD200 | CD200 acts as an important molecule in controlling autoimmunity, inflammation and adaptive immune responses implicating it as a key immunosuppressive molecule noted in several autoimmune diseases including autoimmune encephalomyelitis (EAE), collagen-induced arthritis (CIA), and autoimmune alopecia. |

Specific examples of how MSC secretome preparations synergistically interact with CBD by providing additional CD200 molecules via uptake of target cells in autoimmune diseases.

Experimental autoimmune encephalomyelitis: EAE is a model of the human disease multiple sclerosis, which results from activation of peripheral T lymphocytes, macrophages, and granulocytes. These activated cells migrate to the Central Nervous System and can lead to microglial activation, tissue damage, and neurological deficits including paralysis. In these EAE mice, loss of CD200 resulted in an increase of disease onset and progression compared to mice expressing the gene. Using cultured rat hippocampal neurons, it was found that if the CD200-CD200R signaling pathway is blocked using an anti-CD200R-Fc antibody, the INF-gamma induced IL6 response of macrophages is increased, and macrophage-mediated cell death of the neurons occurred.

Collagen-induced arthritis (CIA): CIA is a model of human rheumatoid arthritis which is an inflammatory autoimmune disease of the joints, and like EAE involves tissue-specific influx of T cells, macrophages, and granulocytes. Disruption of CD200-CD200 receptor interaction using cd200 KO mice increased susceptibility to mice normally resistant to this disease. The animals developed moderate to severe arthritis with synovial inflammation and formation of invasive pannus which results in degradation of cartilage and bone.

Skin Graft Rejection/Transplantation. Experiments from mice have demonstrated that when wild-type tail skin from a male mouse was grafted onto the flank of a strain matched female, the skin was rejected at 59 days. However, if the male skin was CD200-deficient, it was only rejected after only 25 days.

Alopecia (Hair Loss) When expression of CD200 is lost from follicular keratinocytes the CD200R-positive cells (Langerhans cells and dendritic cells) switch to having an activated phenotype. Any additional trauma to the skin can initiate a full activation of CD200 positive cells and cause folliculocentric inflammation. The chronic inflammation that ensues leads to recruitment and activation of autoreactive T cells which are specific for hair follicles and lead to their destruction.

The MSC secretome preparation initiates complimentary regulatory pathways that provide synergistic support of cannabinoid agonist action. For example, CBD is noted to have a role in relieving chronic pain disease symptoms. Cannabinoids act via cannabinoid receptors, but they also affect the activities of many other receptors, ion channels and enzymes. Preclinical studies in animals using both pharmacological and genetic approaches have increased the understanding of the mechanisms of cannabinoid-induced analgesia and provided therapeutic strategies for treating pain in humans. The mechanisms of the analgesic effect of cannabinoids include inhibition of the release of neurotransmitters and neuropeptides from presynaptic nerve endings, modulation of postsynaptic neuron excitability, activation of descending inhibitory pain pathways, and reduction of neural inflammation.

"Characteristic features of neuroinflammation in chronic pain conditions include infiltration of immune cells into the PNS [e.g., the sciatic nerve and dorsal root ganglion (DRG)], activation of glial cells such as microglia and astrocytes in the CNS (spinal cord and brain), and production and secretion of pro-inflammatory cytokines and chemokines [TNF, interleukin (IL)-1β, IL-6, CCL2, and CXCL1]."

In this example, while CBD interactions directly on neurons, the MSC secretome preparation promote reduction of the causative inflammation by decreasing levels of the proinflammatory proteins listed above. MicroRNA content within the exosome subpopulation of the EVs in the MSC secretome preparation has been characterized. MicroRNA function by inhibiting the translation of mRNA into protein. Several miRNA sequences have been identified as present within the MSC secretome preparation which are known to inhibit the proinflammatory proteins, tumor necrosis factor alpha (TNF-α) and Interleukin six (IL-6). The identity and associated function of these miRNAs are listed in Table 2.

TABLE 2

MiRNAs expressed in Extracelluar vesicles (EVs) from bone-marrow mesenchymal stem/stromal cells involved in reducing chronic pain disease related pro-inflammatory molecules.

| miRNA Identity | Function |
|---|---|
| hsa-let-7a-5p | Inhibits IL-6 protein expression |
| hsa-let-7b-5p | |
| hsa-let-7c-5p | |
| hsa-let-7g-5p | |
| hsa-let-7i-5p | |
| hsa-miR-663a | |
| hsa-miR-130a-3p | Inhibits TNF-alpha expression |
| hsa-miR-181a-5p | |

Complimentary mechanisms of action between the MSC secretome preparation and CAs accelerate resolution of chronic pain and inflammation by disrupting cyclic signaling pathways within the target cells that perpetuate the disease state.

H. REFERENCES

Vačković S, Srebro D, Vitiović K S, Vučetić Č, Prostran M. Canriabinoids and Pain: New Insight, From Old Molecules. Front Pharmacol. 2018 Nov. 13; 9:1259. doi: 10.3389/fphar.2018.01259. PMID: 30542280; PMCID: PMC6277878.

Xiaoming Yang, Marpe Bam, Prakash S. Nagarkatti & Mitzi Nagarkatti. Cannabidiol Regulates Gene Expression in Encephalitogenic T cells Using Histone Methylation and noncoding RNA during Experimental Autoimmune Encephalomyelitis. 2019.

What is claimed is:

1. A composition comprising:
   i) a mesenchymal stem cell (MSC) secretome preparation comprising MSC growth factors, MSC extracellular vesicles, MSC exosomes, and/or MSC extracts; and
   ii) a cannabinoid;
   wherein the MSC growth factors, MSC extracellular vesicles, MSC exosomes, and/or MSC extracts are obtained from human bone-marrow MSCs cultured under conditions comprising about 0.1% to about 5% oxygen and an acidic pH of 6.2 to 6.9.

2. The composition of claim 1, wherein the cannabinoid is cannabidiol (CBD) or Cannabigerol (CBG).

3. A method of treating an inflammatory condition, an autoimmune disease, an autoinflammatory disease, metabolic disorder, or inflammation in a subject, the method comprising administering to the subject a therapeutically effective amount of the composition of claim 1.

4. A method of treating an inflammatory condition, an autoimmune disease, an autoinflammatory disease, or metabolic disorder, in a subject, the method comprising culturing bone-marrow mesenchymal stem cells (MSCs) under conditions comprising about 0.1% to about 5% oxygen and an acidic pH of 6.2 to 6.9 to generate a mesenchymal stem cell (MSC) secretome preparation, and administering to the subject a therapeutically effective amount of the MSC secretome preparation and a cannabinoid.

5. The method of claim 4, wherein the MSC secretome preparation and the cannabinoid are administered in the same composition.

6. The method of claim 4, wherein the MSC secretome preparation is administered via inhalation.

7. The method of claim 4, wherein the MSC secretome preparation and the cannabinoid are administered via inhalation.

8. A method of treating inflammation in a subject, the method comprising culturing bone-marrow mesenchymal stem cells (MSCs) under conditions comprising about 0.1% to about 5% oxygen and an acidic pH of 6.2 to 6.9 to generate a mesenchymal stem cell (MSC) secretome preparation and administering to the subject a therapeutically effective amount of the MSC secretome preparation and a cannabinoid.

* * * * *